United States Patent
Pulitzer et al.

(10) Patent No.: US 11,599,908 B2
(45) Date of Patent: *Mar. 7, 2023

(54) SYSTEM AND METHOD FOR ADVERTISING IN RESPONSE TO DIAGNOSTIC TEST

(71) Applicant: RELIANT IMMUNE DIAGNOSTICS, LLC, Austin, TX (US)

(72) Inventors: Jovan Hutton Pulitzer, Frisco, TX (US); Henry Joseph Legere, III, Austin, TX (US)

(73) Assignee: RELIANT IMMUNE DIAGNOSTICS, INC., Austin, TX (US)

( * ) Notice: Subject to any disclaimer, the term of this patent is extended or adjusted under 35 U.S.C. 154(b) by 698 days.

This patent is subject to a terminal disclaimer.

(21) Appl. No.: 15/842,722

(22) Filed: Dec. 14, 2017

(65) Prior Publication Data

US 2018/0174194 A1 Jun. 21, 2018

Related U.S. Application Data

(60) Provisional application No. 62/434,284, filed on Dec. 14, 2016.

(51) Int. Cl.
*G16H 10/40* (2018.01)
*G06Q 30/0251* (2023.01)
(Continued)

(52) U.S. Cl.
CPC ....... *G06Q 30/0267* (2013.01); *A61B 5/0022* (2013.01); *A61B 5/021* (2013.01);
(Continued)

(58) Field of Classification Search
None
See application file for complete search history.

(56) References Cited

U.S. PATENT DOCUMENTS 5,587,061 A 12/1996 Chen
5,709,788 A 1/1998 Chen
(Continued)

FOREIGN PATENT DOCUMENTS

CN 105954512 A 9/2016
EP 2404673 A1 1/2012
(Continued)

OTHER PUBLICATIONS

Brown, M. C. et al. (2009). Lateral Flow Immunoassay. Tse, H. Y., Wong, R. C. (Eds.). New York, NY: Humana Press.
(Continued)

*Primary Examiner* — Robert W Morgan
*Assistant Examiner* — Andrew E Lee
(74) *Attorney, Agent, or Firm* — Gregory M. Howison

(57) ABSTRACT

A system and method are provided for collection and testing of a biologic sample in a self-diagnostic test. The system and method comprise collecting by a user of a testing device a biologic sample for use with the testing device, assigning correlative values as test results, and receiving the test results at a server disposed on a network. Some aspects include a mobile application operating on a mobile device with which the user interacts. These aspects allow advertisements and other messages to be presented to the user through the mobile application. Some aspects present different messages to the user based on the type of self-diagnostic test the user is conducting.

14 Claims, 27 Drawing Sheets

(51) Int. Cl.

| | |
|---|---|
| *G16H 30/40* | (2018.01) |
| *G16H 50/20* | (2018.01) |
| *A61B 5/15* | (2006.01) |
| *A61B 5/00* | (2006.01) |
| *G08B 21/02* | (2006.01) |
| *A61B 5/145* | (2006.01) |
| *H04L 67/04* | (2022.01) |
| *A61B 5/021* | (2006.01) |
| *A61B 5/1468* | (2006.01) |
| *G08B 25/14* | (2006.01) |
| *G08B 5/36* | (2006.01) |
| *G16H 50/70* | (2018.01) |
| *G16H 40/63* | (2018.01) |
| *G16H 40/67* | (2018.01) |
| *H04M 1/72439* | (2021.01) |
| *G06V 10/94* | (2022.01) |
| *G06V 10/24* | (2022.01) |
| *G06V 20/20* | (2022.01) |
| *G06Q 50/22* | (2018.01) |
| *G06F 3/0482* | (2013.01) |
| *H04L 67/01* | (2022.01) |

(52) U.S. Cl.
CPC ........ *A61B 5/1468* (2013.01); *A61B 5/14507* (2013.01); *A61B 5/14532* (2013.01); *A61B 5/14546* (2013.01); *A61B 5/150022* (2013.01); *A61B 5/150358* (2013.01); *A61B 5/150809* (2013.01); *A61B 5/150824* (2013.01); *A61B 5/150854* (2013.01); *A61B 5/4343* (2013.01); *A61B 5/7275* (2013.01); *A61B 5/746* (2013.01); *A61B 5/7435* (2013.01); *A61B 5/7475* (2013.01); *G06V 10/245* (2022.01); *G06V 10/95* (2022.01); *G06V 20/20* (2022.01); *G08B 5/36* (2013.01); *G08B 21/02* (2013.01); *G08B 25/14* (2013.01); *G16H 10/40* (2018.01); *G16H 30/40* (2018.01); *G16H 40/63* (2018.01); *G16H 40/67* (2018.01); *G16H 50/20* (2018.01); *G16H 50/70* (2018.01); *H04L 67/04* (2013.01); *H04M 1/72439* (2021.01); *A61B 5/6898* (2013.01); *G06F 3/0482* (2013.01); *G06Q 50/22* (2013.01); *H04L 67/01* (2022.05); *Y02A 90/10* (2018.01)

(56) References Cited

U.S. PATENT DOCUMENTS

| | | |
|---|---|---|
| 5,876,926 A | 3/1999 | Beecham |
| 5,904,826 A | 5/1999 | Chen |
| 6,149,865 A | 11/2000 | Hsu |
| 7,090,802 B1 | 8/2006 | Wang |
| 7,235,098 B2 | 6/2007 | Palmaz |
| 8,033,460 B2 | 10/2011 | Barnes et al. |
| 8,046,242 B1 | 10/2011 | daCosta et al. |
| 8,177,122 B2 | 5/2012 | Dravnieks et al. |
| 8,308,452 B2 | 11/2012 | Amirouche et al. |
| 8,423,387 B1 | 4/2013 | Mirza |
| 8,506,901 B2 | 8/2013 | Chen et al. |
| 8,548,828 B1 | 10/2013 | Longmire |
| 8,655,009 B2 | 2/2014 | Chen et al. |
| 8,807,169 B2 | 8/2014 | Amirouche et al. |
| 8,877,140 B2 | 11/2014 | Chen et al. |
| 8,911,679 B2 | 12/2014 | Chen et al. |
| 9,285,323 B2 | 3/2016 | Burg et al. |
| 9,311,520 B2 | 4/2016 | Burg et al. |
| 9,390,237 B2 | 6/2016 | Myers et al. |
| 9,523,358 B2 | 12/2016 | Amirouche et al. |
| 9,569,858 B2 | 2/2017 | Babcock et al. |
| 9,607,380 B2 | 3/2017 | Burg et al. |
| 9,726,161 B2 | 8/2017 | Kim et al. |
| 10,818,379 B2 * | 10/2020 | Krishnan ......... G01N 27/44791 |
| 2002/0120466 A1 | 8/2002 | Finn |
| 2002/0134682 A1 | 9/2002 | Chen |
| 2003/0207458 A1 | 11/2003 | Sookbumroong |
| 2005/0266582 A1 | 12/2005 | Modlin et al. |
| 2006/0014302 A1 | 1/2006 | Martinez |
| 2006/0222567 A1 | 10/2006 | Kloepfer et al. |
| 2006/0245933 A1 | 11/2006 | Balch |
| 2007/0196871 A1 | 8/2007 | Reich |
| 2008/0058678 A1 * | 3/2008 | Miyata ................. A61B 5/1519 600/583 |
| 2008/0070599 A1 | 3/2008 | Apodaca |
| 2008/0118397 A1 | 5/2008 | Slowey |
| 2009/0298191 A1 | 12/2009 | Whitesides et al. |
| 2009/0319295 A1 | 12/2009 | Kass-Hout et al. |
| 2011/0045515 A1 | 2/2011 | Bell et al. |
| 2011/0077971 A1 | 3/2011 | Surwit |
| 2011/0115000 A1 | 5/2011 | Yang |
| 2011/0225000 A1 | 9/2011 | Selim |
| 2012/0082598 A1 | 4/2012 | Baydoun |
| 2012/0123686 A1 * | 5/2012 | Xiang ............. G01N 33/48792 702/19 |
| 2012/0176487 A1 | 7/2012 | Pinard et al. |
| 2013/0161190 A1 | 6/2013 | Ewart et al. |
| 2013/0189794 A1 | 7/2013 | Emeric et al. |
| 2013/0203043 A1 | 8/2013 | Ozcan et al. |
| 2013/0273528 A1 | 10/2013 | Ehrenkranz |
| 2014/0051173 A1 | 2/2014 | Barstis et al. |
| 2014/0072189 A1 | 3/2014 | Jena |
| 2014/0072201 A1 | 3/2014 | Tilt |
| 2014/0088991 A1 * | 3/2014 | Bakes ................... G16H 80/00 705/2 |
| 2014/0089006 A1 | 3/2014 | Abreu |
| 2014/0121487 A1 * | 5/2014 | Faybishenko ......... G16H 40/63 600/365 |
| 2014/0154789 A1 * | 6/2014 | Polwart .............. G01N 21/8483 422/403 |
| 2014/0170679 A1 | 6/2014 | Aitchison |
| 2014/0242612 A1 | 8/2014 | Wang et al. |
| 2014/0246334 A1 | 9/2014 | Bosch et al. |
| 2015/0056719 A1 | 2/2015 | Karlovac |
| 2015/0227708 A1 | 8/2015 | Jung |
| 2015/0268186 A1 * | 9/2015 | Pagels ............. G01N 33/48792 205/792 |
| 2015/0308961 A1 | 10/2015 | Burg et al. |
| 2015/0359458 A1 | 12/2015 | Erickson et al. |
| 2016/0077091 A1 | 3/2016 | Tyrrell et al. |
| 2016/0080548 A1 | 3/2016 | Erickson et al. |
| 2016/0103966 A1 | 4/2016 | Mirza |
| 2016/0125600 A1 * | 5/2016 | Lee ........................ G06T 7/90 382/128 |
| 2016/0157789 A1 | 6/2016 | Nicolaus |
| 2016/0162654 A1 * | 6/2016 | Gokhale ............... G16H 10/40 422/402 |
| 2016/0187263 A1 * | 6/2016 | Brown ................. G16H 10/40 348/207.11 |
| 2016/0223536 A1 | 8/2016 | Johnson et al. |
| 2016/0292378 A1 | 10/2016 | Saric |
| 2016/0349185 A1 * | 12/2016 | Park ................... G01N 21/8483 |
| 2016/0374608 A1 | 12/2016 | Dugan |
| 2017/0046546 A1 | 2/2017 | Gibson |
| 2017/0059566 A1 | 3/2017 | Reed et al. |
| 2017/0089893 A1 | 3/2017 | Legere, III |
| 2017/0153185 A1 * | 6/2017 | Kisner ................ G06V 10/245 |
| 2017/0323431 A1 | 11/2017 | Sarkar et al. |
| 2018/0136140 A1 * | 5/2018 | Brendsel ............... G06T 7/0012 |
| 2020/0168067 A1 | 5/2020 | Takahashi |

FOREIGN PATENT DOCUMENTS

| | | |
|---|---|---|
| WO | 2001050397 A1 | 7/2001 |
| WO | 2010118124 A2 | 10/2010 |
| WO | 2013158504 A1 | 10/2013 |
| WO | 2014080212 A3 | 8/2014 |
| WO | 2015022318 A1 | 2/2015 |
| WO | 2015143309 A1 | 9/2015 |
| WO | 2016188549 A1 | 12/2016 |

(56) References Cited

FOREIGN PATENT DOCUMENTS

OTHER PUBLICATIONS

Baltekin, O., et al. (Aug. 22, 2017) Antibiotic susceptibility testing in less than 30 min using direct single-cell imaging. Proceedings of the National Academy of Sciences. 114(34).
Mudanyali, O. et al. Integrated Rapid-Diagnostic-Test Reader Platform on a Cellphone. Lab on a Chip, vol. 12, No. 15. Aug. 7, 2012; pp. 7, 12.
FisherSCI. Anti-Zika virus ELISA (IgM) test instruction. Sep. 2, 2016.
Acharya, D. et al. An ultrasensitive electrogenerated chemiluminescence-based immunoassay for specific detection of Zika virus. Scientific Reports 6, Article No. 32227. Aug. 2016.
International Search Report and Written Opinion of the International Searching Authority from PCT/US17/57037, dated Dec. 28, 2017.
International Search Report and Written Opinion of the International Searching Authority from PCT/US17/57039, dated Dec. 26, 2017.
International Search Report and Written Opinion of the International Searching Authority from PCT/US17/57041, dated Dec. 14, 2017.
International Search Report and Written Opinion of the International Searching Authority from PCT/US17/60252, dated Jan. 12, 2018.
International Search Report and Written Opinion of the International Searching Authority from PCT/US17/66528, dated Mar. 7, 2018.
Jianjun Li et al. Application of Microfluidic Devices to Proteomics Research. Journal: Molecular & Cellular Proteomics Jan. 3, 2002. 1:157-168. Canada.
Pegah N. Abadian et al. Accepted Manuscript. Book: Analytical Methods. 22pgs. Boston, MA.
Kling A. et al. Electrochemical microfluidic platform for simultaneous multianalyte detection Article, 2015, 916-919, Europe.
Andre Kling et al. Multianalyte Antibiotic Detection on an Electrochemical Microfluidic Platform. Article. Jul. 19, 2016, 10036-10043, Germany.
Mercier Marco. Microfluidic Continuous Flow Cell Counting and Concentration. Article. 10pgs.
Meichei Wang Kadlec et al. A Cell Phone-Based Microphotometric System for Rapid Antimicrobial Susceptibility Testing. Journal. 2014, vol. 19 (3) 258-266. Tucson, AZ.
Hongying Zhu et. al. Cost- effective and compact wide-field fluorescent imaging on a cell-phone. Article. Jan. 21, 2011. 315-322, 11(2). California.
Moffitt Jeffrey R. et al. The single-cell chemostat: an agarose-based, microfluidic device for high-throughput, single-cell studies of bacteria and bacterial communities. Article. Oct. 24, 2017. 21pgs. 12(8).
Temiz Yuksel et al. Microelectronic Engineering. Article. 2015. 156-175. Published by Elsevier B.V. Switzerland.
Vasdekis Andreas et al. Review of methods to probe single cell metabolism and bioenergetics, Journal, Jan. 20151. 115-135. Published by Elsevier.
Wang Shuqi et al. Portable microfluidic chip for detection of *Escherichia coli* produce and blood. International Journal of Nanomedicine. May 27, 2012. 2012:7 2591-2600. MA.
Hoylandm James Donaldson. Microfluidic chip and connector. Nov. 11, 2012, 16pgs. Europe.
Baltekin Ozden et al. Antibiotic susceptibility testing in less than 30 min using direct single-cell imaging. Aug. 22, 2017. 9170-9175 vol. 114-34.
Ashraf Muhammad Waseem. Micro Electromechanical Systems (MEMS) Based Microfluidic Devices for Biomedical Applications Journal : Molecular Sciences Jun. 7, 2011. 3648-3704.
Radenovic Aleksandra. Advanced Bioengineering Methods Laboratory Microfluidics Lab on Chip. 27pgs.
J. Hassan et al., A microfluidic biochip for complete blood cell counts at the point-of-care, Dec. 2015, 201-213, 3(4).
Kling Andre et al, Multianalyte Antibiotic Detection on an Electrochemical Microfluidic Platform, 1-3 pgs. Germany.
Au K. Anthony et al, Microvalves and Micropumps for BioMEMS, May 24, 2011, 179-220.
Sticker Drago et al., Multi-layered, membrane-integrated microfluidics based on replica molding of a thiol-ene epoxy thermoset for . . . Article, Nov. 2015, 4542-4554.
Shaegh et al., Plug-and-play microvalve and micropump for rapid integration with microfluidic chips, Article, Apr. 22, 2015, 557-564, Massachusetts, Springer Berlin Heidelberg.
Schaler Dawn et al, Microfluidic cell counter with embedded optical fibers fabricated by femtosecond laser ablation and anodic bonding, Article, Apr. 13, 2009, 17(8), 6068-6073, Colorado.
Hassan U. et al, A microfluidic biochip for complete blood cell counts at the point-of-care, Dec. 2015, 201-213. 3(4).
Feng, S., Caire, R., Cortazar, B., Turan, M., Wong, A., & Ozcan, A. (2014). Immunochromatographic diagnostic test analysis using-Google Glass ACS nano, 8(3), 3069-3079 (Year: 2014).
Lee, S., O'Dell, D., Hohenstein, J. et al. NutriPhone: a mobile platform for low-cost point-of-care quantification of vitamin B12 concentrations. Sci Rep 6, 28237 (2016) doi: 1 0.1 038/srep28237 (Year: 2016).
Pakhomov, S. V. S., Buntrock, J. D., & Chute, C. G. (2006). Automating the Assignment of Diagnosis Codes to Patient Encounters Using Example-based and Machine Learning Techniques. Journal of the American Medical Informatics Association, 13(5),516-525 doi: 1 0.1197/jarnia.m2077 (Year: 2006).
Patent Cooperation Treaty: International Preliminary Report on Patentability of PCT/US2017/066518 (related application); Agnes Wittmann-Regis; Jun. 18, 2019; 5 pages.

* cited by examiner

| BIOLOGIC ID # 2402 | | |
|---|---|---|
| BIOLOGIC TYPE | BLOOD | |
| PREGNANCY RATING | 99 | |
| ZIKA INFECTION RATING | 75 | |
| GLUCOSE RATING | 10 | |

SYSTEM AND METHOD FOR ADVERTISING IN RESPONSE TO DIAGNOSTIC TEST

CROSS-REFERENCE TO RELATED APPLICATIONS

This application claims the benefit of U.S. Provisional Application No. 62/434,284, filed on Dec. 14, 2016, entitled SYSTEM AND METHOD FOR ADVERTISING IN RESPONSE TO DIAGNOSTIC TEST, which is incorporated by reference herein in its entirety.

TECHNICAL FIELD

The following disclosure is related to biologic self-diagnostic testing and, more specifically, to delivering advertising messages to users of mobile applications used for self-diagnostic testing.

BACKGROUND

When using a mobile application to conduct self-diagnostic testing on biologic materials, a user may have opportunities to view messages within the mobile application. Therefore, what is desirable is a system and method for delivering messages and advertisements to a user through a mobile application.

SUMMARY

In one aspect thereof, a system and method are provided for collection and testing of a biologic sample in a self-diagnostic test. The system and method comprise collecting by a user of a testing device a biologic sample for use with the testing device, assigning correlative values as test results, and receiving the test results at a server disposed on a network. Some aspects include a mobile application operating on a mobile device with which the user interacts. These aspects allow advertisements and other messages to be presented to the user through the mobile application. Some aspects present different messages to the user based on the type of self-diagnostic test the user is conducting.

BRIEF DESCRIPTION OF THE DRAWINGS

For a more complete understanding, reference is now made to the following description taken in conjunction with the accompanying Drawings in which.

DETAILED DESCRIPTION

Figure 1:
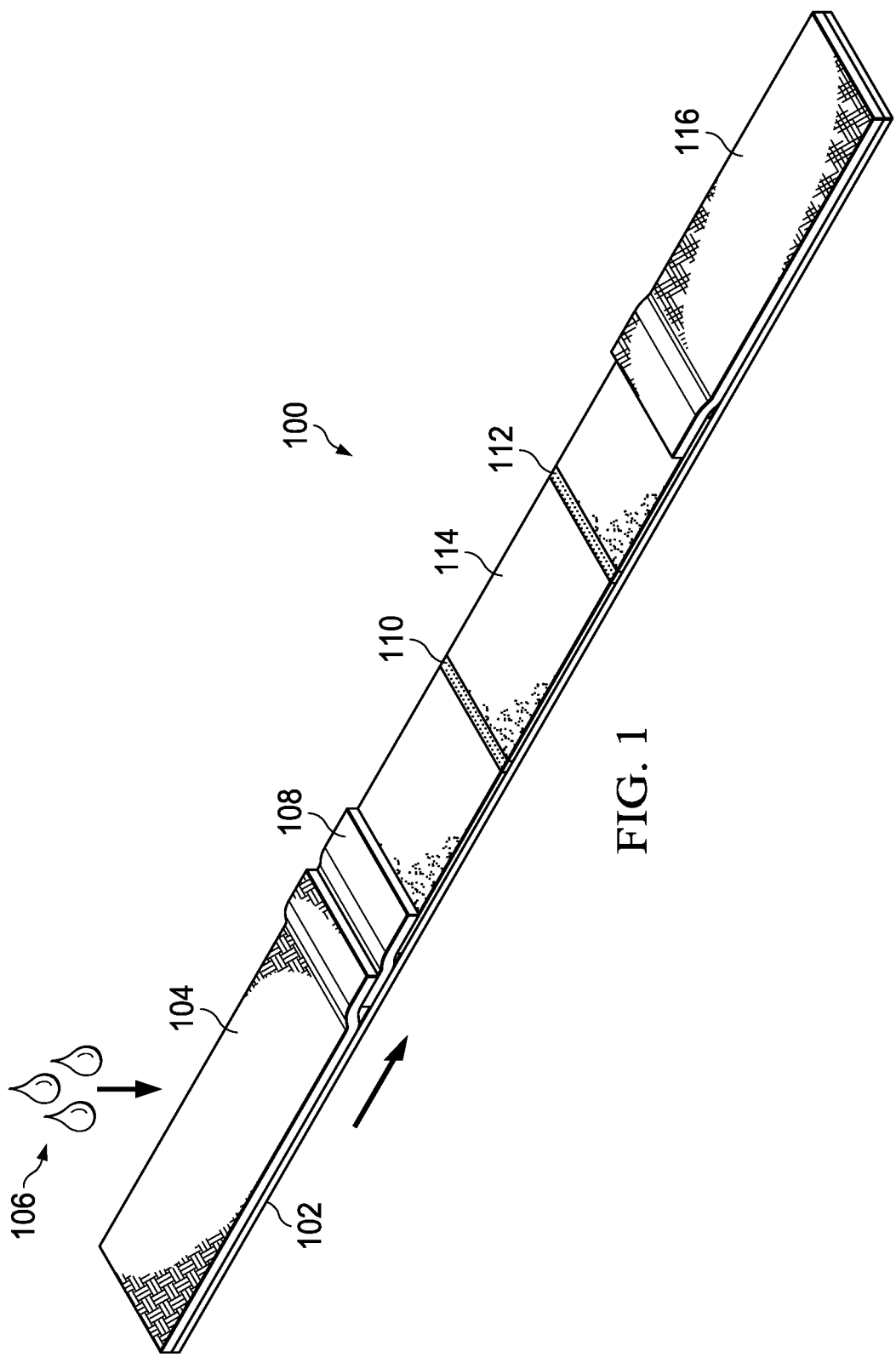
FIG. 1 illustrates a diagrammatic representation of one embodiment of a immunoassay test strip.

Referring now to the drawings, wherein like reference numbers are used herein to designate like elements throughout, the various views and embodiments of an arbovirus indicative birth defect risk test are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to FIG. 1, there is illustrated one embodiment of an immunoassay test strip 100. The test strip 100 is typically housed in a testing device configured to collect a biologic analyte 106 from a user and to direct to the biologic analyte 106 onto the testing strip 100. However, it will be understood that the biologic may be applied onto a strip 100 without the strip 100 needing to be within a testing device. The test strip 100 includes a backing 102. The test strip 100 is made up of multiple sections disposed on the backing 102. A sample pad 104 is disposed on one end of the strip 100, for collecting the biologic analyte 106. The biologic analyte 106 may be any biologic needed for use in the immunoassay, such as urine, blood, saliva, stool, sweat, or other biologics to be used as an analyte. Various methods may be used to acquire the needed biologic, and such may be provided to the user packaged with the test, such as swabs, vials, containers, dilutants and other solutions, or any other equipment required. In the case of a blood analyte, a few drops of blood may be obtained from a finger stick using a finger prick device. Such a blood analyte may be blood mixed with an adequate amount of buffered solution to create the sample analyte 106 or a blood sample that is not diluted or otherwise manipulated, in which case the blood only is the analyte 106.

The biologic analyte 106, after coming into contact with the sample pad 104, begins to migrate across the strip 100 by capillary action, coming into contact with other sections of the strip 100. A particle conjugate pad 108 is disposed between the sample pad 104 and a test line 110. The conjugate pad 108 may contain various reagents associated with a particular antigen, such as a virus, allergen, or bacteria, the reagents being items such antibodies, enzymes, or other reagents needed to diagnose the particular condition. The reagent in the conjugate pad 108 may be conjugated with particles of materials such as colloid gold or colored latex beads. As the analyte 106 migrates through the conjugate pad 108, antibodies present in the sample analyte 106 complex with the reagents in the conjugate pad 108, thereby creating an immune complex that will migrate to the test zone or test line 110.

The test line 110 (T) may be precoated with the relevant antigen in question, i.e., a virus, allergen, or bacteria, for the detection of antibodies associated with the particular antigen. The immune complex created when the analyte 106 passes through the conjugate pad 108 is captured onto the antigen contained on the test line 110. This may create a qualitative response on the strip where the test line 110 is located, such as a colored response. In some embodiments, the test line 110 may not be a line, but may be other shapes or symbols, such as a plus sign. If no antigen-anti-antigen complexes are present in the analyte, no reaction occurs in the test line 110 and a qualitative response will not occur.

After passing through the test line 110, the analyte migrates further along the strip to reach a control line 112, where excess anti-antibody-colloidal gold or latex conjugates get bound. A qualitative response may be shown at the control line 112, indicating that the sample has adequately migrated across the testing membrane or substrate as intended. It will be understood that the control line 112 is not necessarily needed to perform the test, and may be eliminated entirely, but the control line 112 does provide a comparative example for a user reading the test. For example, the control line 112, in embodiments where a colored qualitative response is provided, may appear as an overly saturated color, such as a dark or bright saturated red, once the sample reaches the control line 112. This saturated color may be used as a comparison against the qualitative response shown on the test line 110. For example, if the qualitative response shown on the test line 110 is a much lighter red than that on the test line 110, it may be that very little reaction occurred at the test line. Of course, if no response is shown at all at the test line 110, no reaction has occurred. If the qualitative response at the test line 110 is of a similar saturation to the control line 112, a strong reaction is indicated.

The strip 100 may not be a continuous substrate. Rather, the various sections of the strip 100 may be separate from each other, but all adhered to the backing 102. As shown in FIG. 1, the sample pad 104 and the conjugate pad 108 are separate structures from each other. The test line 100 or zone and the control line 112 or zone are both disposed as part of a nitrocellulose membrane strip 114. The nitrocellulose membrane strip 114 is also adhered to the backing 102, but separate from the sample pad 104 and the conjugate pad 106. As shown in FIG. 1, the end of the sample pad 104 adjacent to the conjugate pad 106 may overlap the conjugate pad 106, with that end of the sample pad 106 lying over the adjacent end of the conjugate pad 106. Similarly, the end of the conjugate pad adjacent to the nitrocellulose membrane strip 114 may lie over the end of the nitrocellulose membrane adjacent to the conjugate pad. This allows for the analyte 106 to be more easily deposited onto each section of the strip 100 as it migrates across the strip 100. After the analyte 106 migrates across the nitrocellulose membrane strip 114, and thus across the test line 110 and the control line 112, the analyte 106 comes into contact with a wick 116 for absorbtion and collection of the analyte 106. The end of the wick 116 adjacent to the nitrocellulose membrane strip 114 may lie over that adjacent end of the nitrocellulose membrane strip 114, as shown in FIG. 1.

Several Flow Immune Assays have been directed toward identifying proteins, molecules of interest, and even immunoglobulins IgG, IgA, and IgM. IgE is an antibody (immunoglobulin E) that is normally present in the blood freely circulating until it moves into the tissue where it is bound to mast cells through the receptor FcERI (F-C-epsilon-R-one) otherwise known as the high affinity IgE receptor. There is a small amount of IgE bound to IgE receptors (high and low affinity receptors) on basophils, eosinophils, and other cells in the blood and tissues.

Many assay systems are geared toward the detection of infectious proteins. All of the aforementioned tests use a non-human antibody—usually IgG type—e.g., goat IgG antibody directed against a protein of interest to detect the protein of interest from the sample (blood, urine, saliva, sweat, etc.). This antibody complexes with protein of interest and forms a complex that travels across the membrane until it reaches the test zone. In the test zone there is an IgG type antibody directed against IgG from that species of animal. As further described herein, the present detecting apparatus and method use human (patient/consumer-derived) antibodies from the sample and the test zone that contains a humanized antibody directed against the protein of interest that is preconjugated to a detecting substance that results in a visual change.

Summary of Target Antigen

The target antigens may be proteins, glycoproteins, lipoproteins or other molecular substances capable of eliciting an immune reaction and/or being bound by human specific IgE (sIgE).

Immune Assay to Detect Specific IgE

In the detecting apparatus and method of using the same, the antigens are proteins conjugated to a noble metal, for example, gold, or latex conjugated to antigen in the test zone, for the purpose of detecting the presence of specific IgE (e.g., anti-peanut IgE in a blood sample from a finger prick). For example, an IgG class antibody (IgG1, IgG2, IgG3, or IgG4) or fragments of those classes of antibodies (fab fragments) whose origin may be any animal species (goat, rat, human, etc.) capable of detecting human IgE (anti-IgE IgG)—a suitable commercially available humanized antibody, such as omaluzimab may be used—may be used to form immune complexes of IgG-anti-IgE-sIgE that will migrate to the test zone having selected specific IgE that can bind to the conjugated antigen.

Immune Assay to Detect Total IgE (Not Concerned About Specific IgE)

Another embodiment includes using an IgG class antibody (IgG1, IgG2, IgG3, or IgG4) or fragments of those classes of antibodies (fab fragments) whose origin may be any animal species (goat, rat, human, etc.) capable of detecting human IgE (anti-IgE IgG)—a suitable commercially available humanized antibody that is preconjugated to a detecting molecule that results in a color change when bound to IgE as the target antigen in the test zone.

Figure 2:
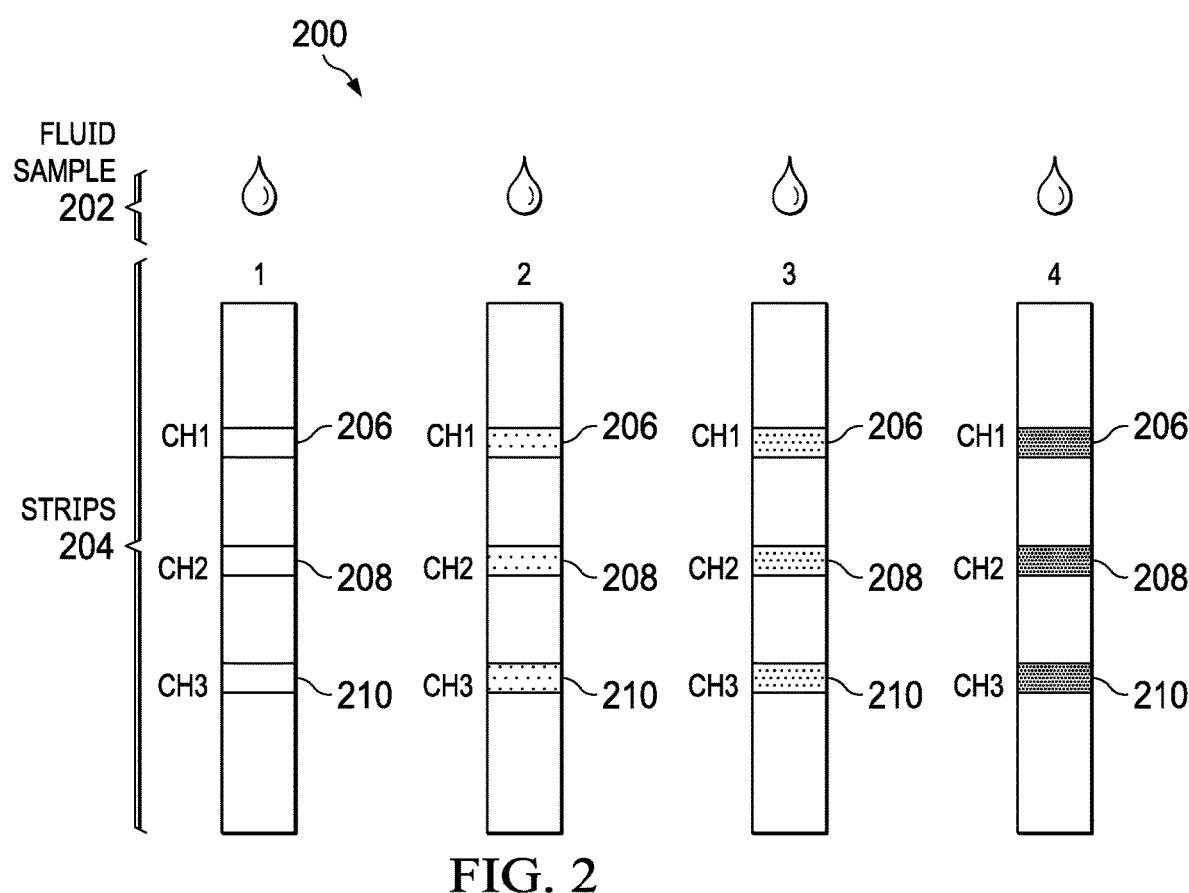
FIG. 2 illustrates a diagrammatic representation of one embodiment of an immunoassay test wherein an analyte is tested across a plurality of test strips.

Referring now to FIG. 2, there is illustrated one embodiment of an immunoassay test 200 wherein an analyte 202 is tested across a plurality of test strips 204. The plurality of test strips 204 may each be configured for testing for a particular antigen. For instance, one strip may be for testing for the presence of streptococcal bacteria (strep throat), one strip may be for testing for a peanut allergy, one strip may be for testing for the Zika virus, etc. Additionally, each strip may also test for multiple antigens. For example, as shown in FIG. 2, multiple testing panels or lines maybe be incorporated. Each line may be for a particular antigen. As shown in FIG. 2, multiple test lines 206, 208, and 208 may be disposed along the plurality of strips 204. A strip testing for allergens may have a panel for testing for peanut allergies shown at test line 206 (CH1), for cat allergies shown at test line 208 (CH2), or grass allergies shown at test line 210 (CH3).

Other examples of configurations for the testing panels can be, but are not limited to: 1) Food 5: Peanut, milk, soy, wheat, egg; 2) Nut and seed panel: almond, cashew, hazelnut, peanut, pecan, walnut, sesame seed, sunflower seed; 3) seafood: crab, lobster, shrimp, salmon, tuna; 4) Pets: cat, dog; 5) Indoor allergens: dust mites, mold mix (alternaria, aspergillus, penicillium, cladosporium), cat, dog; and 6) seasonal allergens: grass (Bermuda, bahia, Johnson, rye, timothy), trees (oak, elm, cedar, mesquite, pine, etc.), weeds (pigweed, ragweed, sage, Russian thistle).

With respect to other non-allergen antigens, the panels may be for testing for strep, Zika, flu, anthrax, cold viruses, cancer, HPV, Lyme disease, mononucleosis (mono), and other illnesses, and/or other conditions such as pregnancy (hCG detection) and disease risks. Some embodiments may allow for the testing of various arboviruses (arthropod-borne viruses). Arboviruses are viruses that are transmitted by arthropods, with mosquitos being a common vector for the virus. Vectors are organisms that transfer the virus from a host that carries the virus. Thus, in the case of mosquitos, a mosquito that feeds on a host that is infected with a virus may infect others when that mosquito again feeds on an uninfected host. Well-known arboviruses include Dengue virus, Japanese encephalitis virus, Rift Valley fever virus, West Nile virus, yellow fever virus, chikungunya, and Zika virus. Urine, blood, and saliva and other biologics may be used for arboviruses testing.

Certain antigens or medical conditions may be logically paired together. For instance, a testing device may include both a strip for detection of pregnancy and a strip for the detection of the zika virus, as the Zika virus has been known to cause birth defects in infants born to pregnant women that are infected with Zika. Thus, combining these two tests into a single testing device or kit would alert a woman to a potential Zika infection proximate in time to the time she also discovers she is pregnant, allowing the woman to seek medical attention immediately. This is a substantial improvement over past Zika testing, where a woman may be required to wait weeks before results are returned from a lab after having the biologic collected by her physician. In many cases, this may lead to a woman having passed a state-mandated cutoff point for abortions, such as 24 weeks in some states. Combining a Zika test with a pregnancy test and physically linking the two tests, and thus allowing for a woman to determine a Zika risk at the time of taking a pregnancy test, in which a pregnancy test may be taken as soon as six days after conception, allows for that woman to take action much sooner than the state mandated cutoff and waiting for lab results would allow.

Various testing devices that include the test strip 100 or strips may be used, such as a slide that supports the test strip 100, a cassette based diagnostic test, a dipstick, or combinations thereof. The test results in various embodiments may be in the form of a visual qualitative reading test, a visual semiquantitative format, a reader quantitative assay format, and/or combinations thereof. Additionally, an electronic implementation may be used where the result is displayed digitally on a screen disposed within the apparatus, and visible to the user.

The apparatus and method of detection may be a "one-step" approach from sample to reading without sample dilution or other sample manipulation. The sample may be diluted or endure other sample manipulation, for example the blood sample is diluted with a buffer.

Figure 3:
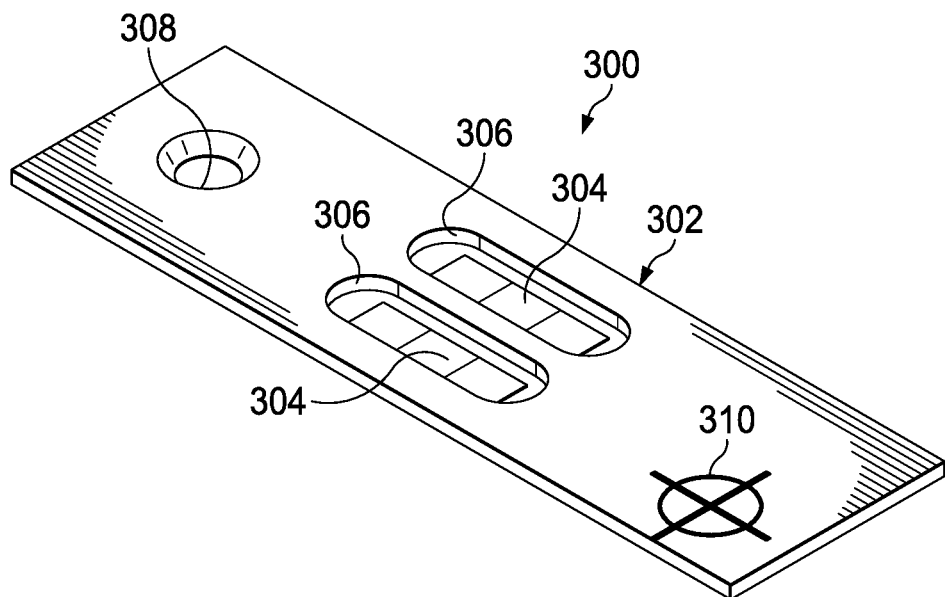
FIG. 3 illustrates a diagrammatic representation of one embodiment of a testing device.

Referring now to FIG. 3, there is illustrated a diagrammatic representation of one embodiment of a testing device 300. The testing device 300 includes a housing 302 that forms the body of the testing device. The housing 302 may be made of plastic, metal, or any material durable enough for shipping and subsequent handling by a user. The housing 302 may be hollow so that a plurality of test strips 304 may be housed within and so that a biologic may be deposited within the housing 302. The testing device 300 may further have a plurality of windows 306, each window being associated with one of the plurality of test strips 304, and allowing for a user to view at least the section of the nitrocellulose membrane strip 114 where the test line 110 and control line 112 are located. The plurality of windows 306 may be open, or covered with plastic, glass, or other materials that allow for viewing the plurality of strips 304. A sample well 308 may be disposed on a surface of the housing 302 to allow a user to deposit a biologic into the housing 302. The sample well 308 would be disposed over or near the sample pad 104 of the test strip or strips 100. In the embodiment shown in FIG. 3, a single sample well 308 is included for collection of a single type of biologic for testing, with each of the plurality of strips 304 being suited for testing for antigens using that particular biologic sample type. For example, if the testing device 300 is a combined pregnancy and Zika test, having both a pregnancy strip and a Zika strip, a urine sample may be deposited into the sample well 308, causing the urine sample to come into contact with the sample pad 104 on both the pregnancy strip and the Zika strip. It will be understood that both of these tests may also be performed with a blood sample.

The testing device 300 may also have disposed on the surface of the housing a crosshair symbol 310, used as an alignment target. This symbol may be a graphic printed or adhered to the testing device 300. The crosshair symbol 310 is used to align the testing device 300 for the taking of an image of the testing device 300 using a camera on a mobile device, for use in a mobile device application described herein. In other embodiments, the crosshair symbol 310 may be other types of symbols, such as a simple shape (circle, square, etc.), other images (such as a medical cross symbol, an arrow, etc.), or any other type of image.

Figure 4:
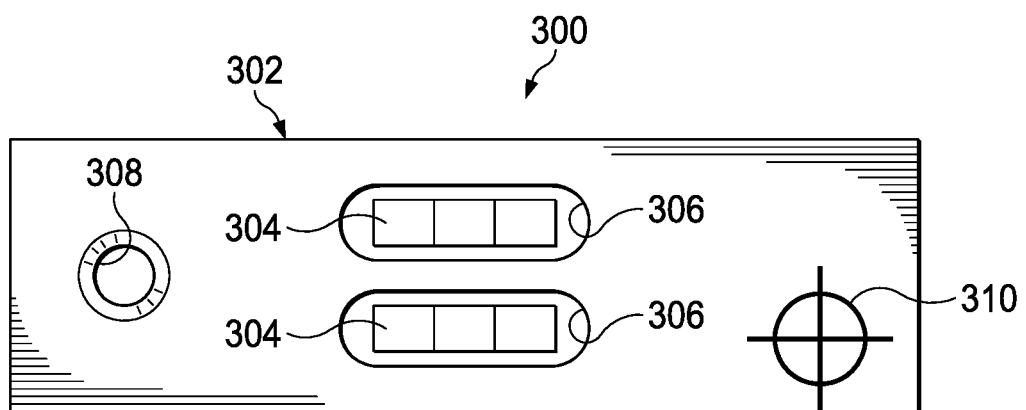
FIG. 4 illustrates a top view of the testing device of FIG. 3.

Referring now to FIG. 4, there is illustrated a top view of the testing device 300. There is again shown the housing 302, the plurality of test strips 304, the plurality of windows 306, the sample well 308, and the crosshair symbol 310.

Figure 5:
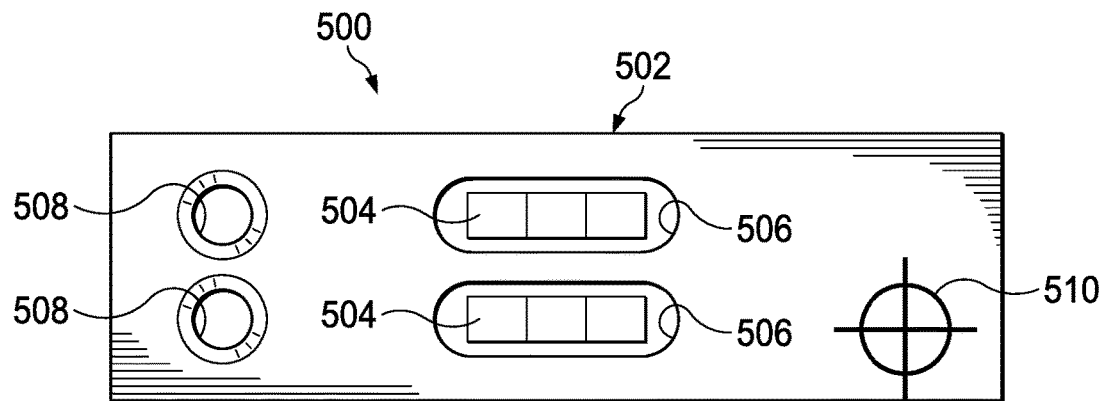
FIG. 5 illustrates a top view of one embodiment of a testing device.

Referring now to FIG. 5, there is illustrated a top view of one embodiment of a testing device 500. The testing device 500 includes a housing 502 having a plurality of test strips 504 within the housing 502 and a plurality of windows 506 for display of the plurality of strips 504. The housing 502 also includes a plurality of sample wells 508 disposed on one side of the testing device 500. Each of the plurality of sample wells 508 is associated with one of the plurality of test strips 504 and each of the plurality of sample wells 508 may be disposed over one of the sample pads 104 on the associated one of the plurality of test strips 504. This allows for a biologic to be deposited into each of the plurality of sample wells 508, with each well 508 serving to transfer the biologic to the test strip underneath the sample well. The testing device 500 further includes a crosshair 510. The crosshair symbol 510 is used to align the testing device 500 for the taking of an image of the testing device 500 using a camera on a mobile device, for use in a mobile device application described herein.

Figure 6:
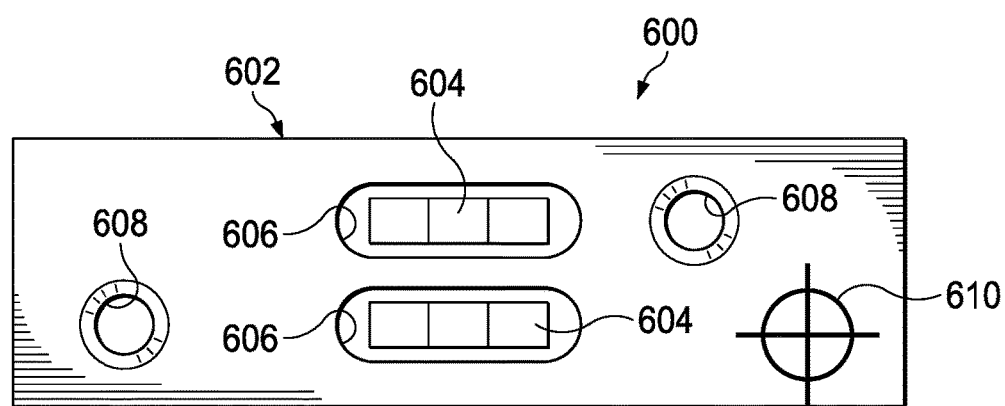
FIG. 6 illustrates a top view of another embodiment of a testing device.

Referring now to FIG. 6, there is illustrated a top view of another embodiment of a testing device 600. The testing device 600 includes a housing 602 having a plurality of test strips 604 within the housing 602 and a plurality of windows 606 for display of the plurality of strips 604. The housing 602 also includes a plurality of sample wells 608. In this embodiment, the sample wells are located on different ends of the housing 602. In the case of a two test strip device, the sample wells 608 are disposed on opposite ends of the testing device 600. The strips 604 would be arranged within the housing in such a way as to allow the sample pad 104 on each of the strip to be disposed underneath one of the sample wells 608. This is useful for testing devices that require different biological samples. For example, if the testing device 600 required a urine sample for one strip and a blood sample for the other strip, having the wells 608 disposed on opposite sides of the testing device would reduce the likelihood that a urine sample, for instance, might be inadvertently deposited into the well designated for the blood sample. In embodiments where there are more than two strips, and more than two wells, the well positions may alternate between the two sides of the testing device. For instance, a first well for a first strip might be disposed on the left side of the testing device, a second well for a second strip might be disposed on the right side of the testing device, a third well for a third strip might be disposed on the left side of the testing device, a fourth well for a fourth strip might be disposed on the right side of the testing device, and so on. The testing device 600 further includes a crosshair 610. The crosshair symbol 610 is used to align the testing device 600 for the taking of an image of the testing device 600 using a camera on a mobile device, for use in a mobile device application described herein.

The diagnostic test can, for example, be produced in a various formats for different users, such as, but not limited to, consumer/in-home use where the test is purchased through retail channels which will allow individuals to get an immediate, cost-effective test result that can lead to specific avoidance and treatment through follow-up with a medical professional.

The diagnostic test can be provided to and used by hospitals and clinics to provide rapid, on-site test results that are required to prescribe certain medications, such as omaluzimab, by their FDA labels.

This diagnostic assay can be modified to detect the presence of specific IgE in pets.

It is also noted that housing 602 is designed such that both strips 604 are disposed in physical proximity thereto and in the same actual housing. In this manner, both sets are linked physically to each other such that they cannot be separated and can be associated with a single individual and the actual test cannot be separated. As such, when a patient applies the specimens to the two areas 608 and the test results are exhibited, there is a high probability that two tests were performed at the same time associated with the same patient. Additionally, and electronic chip (not shown) can be embedded within the housing 602 such that the housing 602 can be registered to a specific patient and associated with the medical records of that patient.

Figure 7:
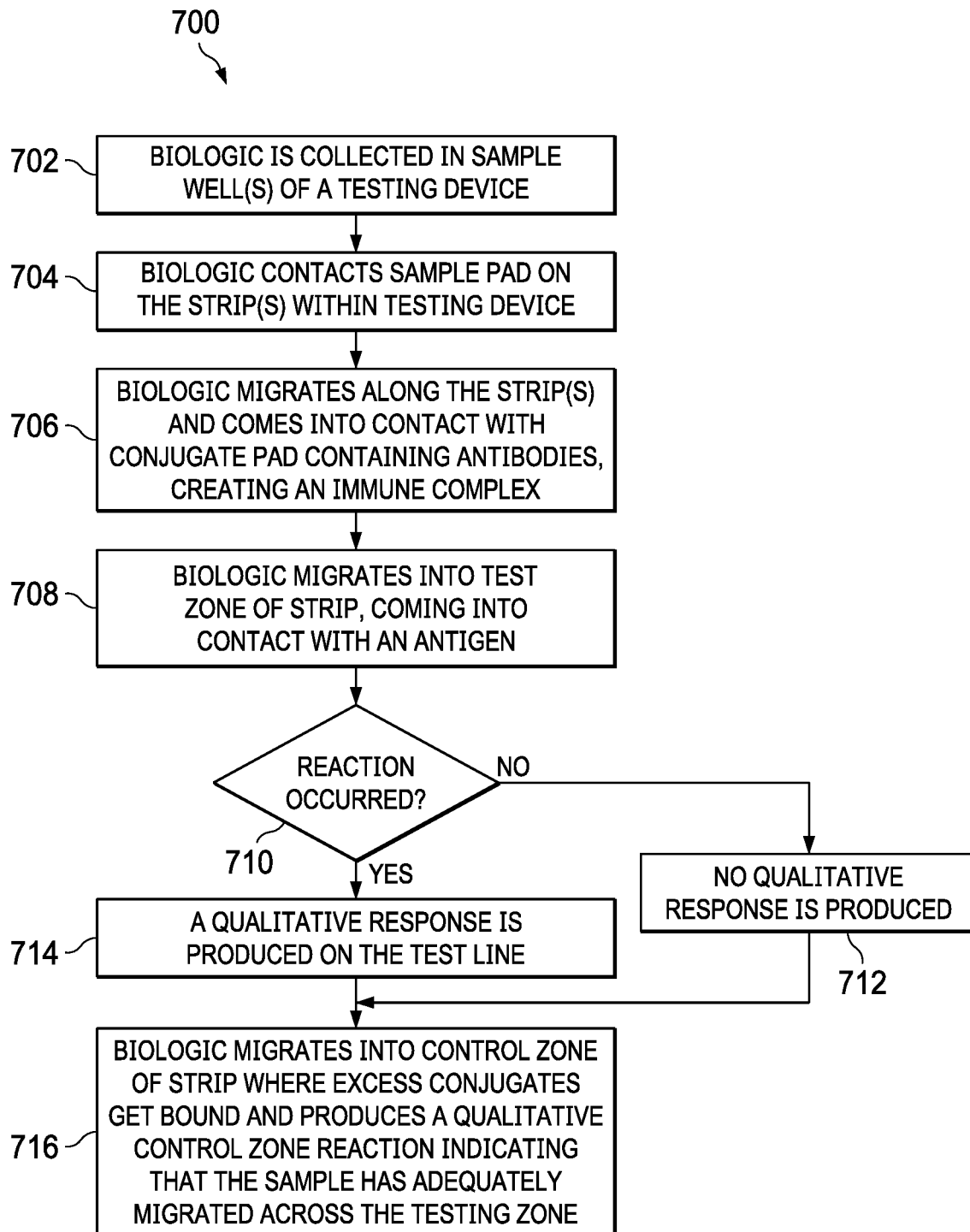
FIG. 7 illustrates a flowchart of one embodiment of a testing device use method.

Referring now to FIG. 7, there is illustrated a flowchart of one embodiment of a testing device use method 700. The method 700 begins at step 702 where a biologic is collected in a sample well or wells of a testing device. The biologic collected may be a non-diluted or non-manipulated biologic, such as blood, urine, or saliva from the user of the test. Diluted or manipulated biologics may be used instead, as required by the specific test. For example, if a viral test requires the biologic to be added to a solution, the biologic could be added to a solution that has previously been placed in a sterilized vial provided with the testing device. After the required amount of time has passed, the solution containing the biologic could be deposited into the well or wells. At step 704, the biologic contacts a sample pad disposed on a strip or strips within the testing device. At step 706, the biologic migrates along the strip or strips to come into contact with a conjugate pad containing antibodies. Antibodies present in the biologic will complex with the antibodies in the conjugate pad to create an immune complex. At step 708, the biologic migrates into a test zone of the strip or strips, coming into contact with an antigen. The antibodies in the conjugate pad serve to provide a means of detection, such as a colored response, if the immune complex binds with the antigen present in the test zone of the strip. At decision block 710, binding of the antibodies with the antigen may or may not occur depending on if antibodies associated with the antigen are present in the biologic or not. If a binding between the antibodies and the antigen does not occur the process moves to step 712 where no qualitative response is produced on the test line. If a binding does occur, at step 714 a qualitative response is produced on the test line. Whether a binding occurs or not, and whether a qualitative response is produced or not, the process moves to step 716 where the biologic migrates into a control zone of the strip or strips where excess conjugates get bound and produces a qualitative control zone reaction indicating that the sample has adequately migrated across the testing zone.

It will be understood by one skilled in the art that the antibodies and antigens applied to the testing strip may be altered depending on the type of condition being tested. For example, in the case of testing for medical conditions that do not involve an illness or infection, like pregnancy, and thus the sample biologic does not contain antibodies associated with the condition, antibodies that react to markers being tested for may be applied to the testing strip instead of an antigen. For instance, pregnancy test requires testing for the presence of hCG. Since hCG is a hormone and not an antibody produced in response to an infection, the testing strip may have antibodies that will react to the presence of hCG applied to the testing zone or line of the testing strip, as well as to the conjugate pad. Similarly, some tests might require antibodies be applied to the testing strip to detect antigens present in the sample, rather than antibodies.

Figure 8A:
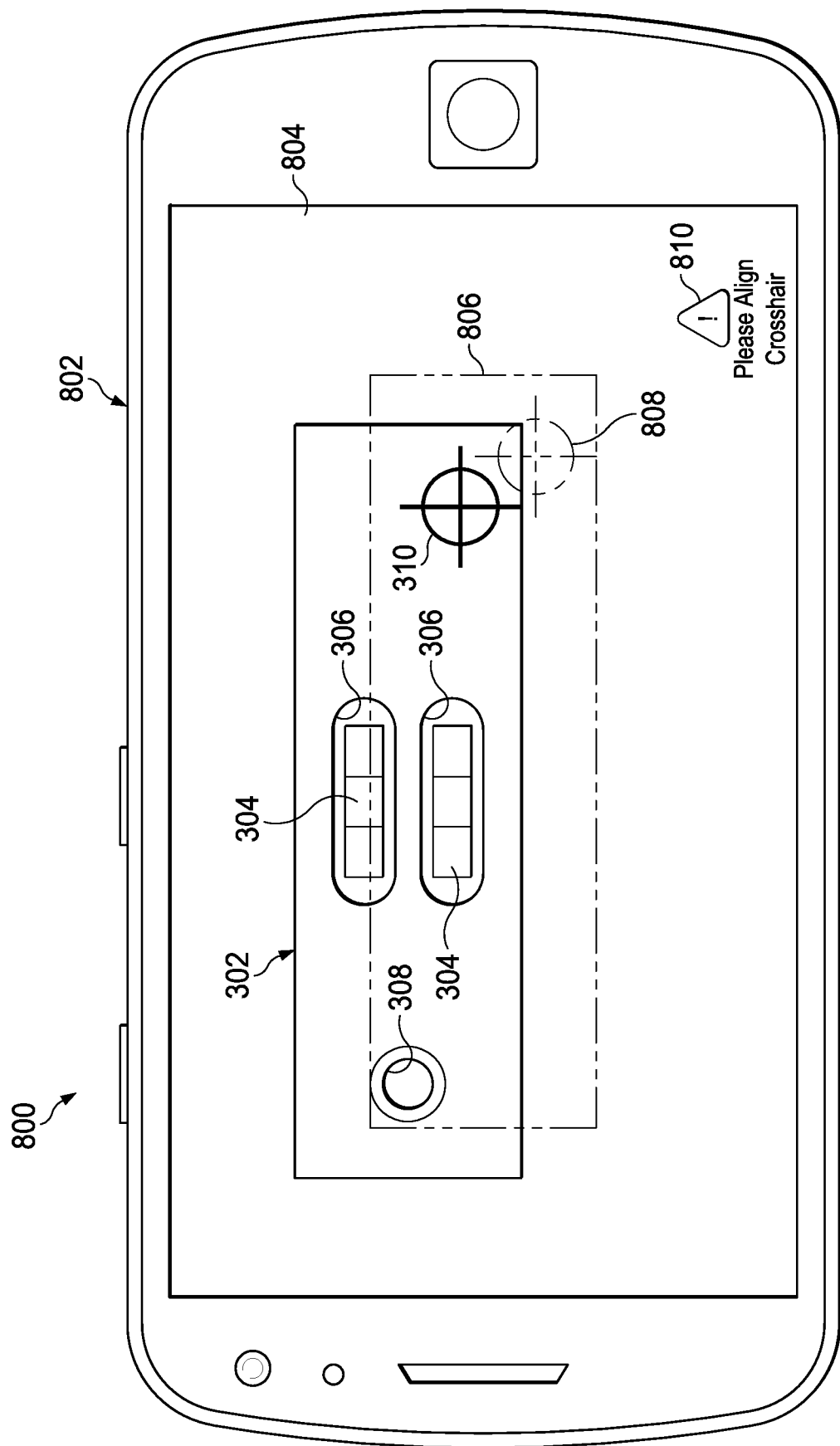
FIG. 8A illustrates a diagrammatic representation of one embodiment of a process for a mobile device application for testing device image capture and image processing, wherein an image alignment indicator is not aligned with the subject of the image.
Figure 8B:
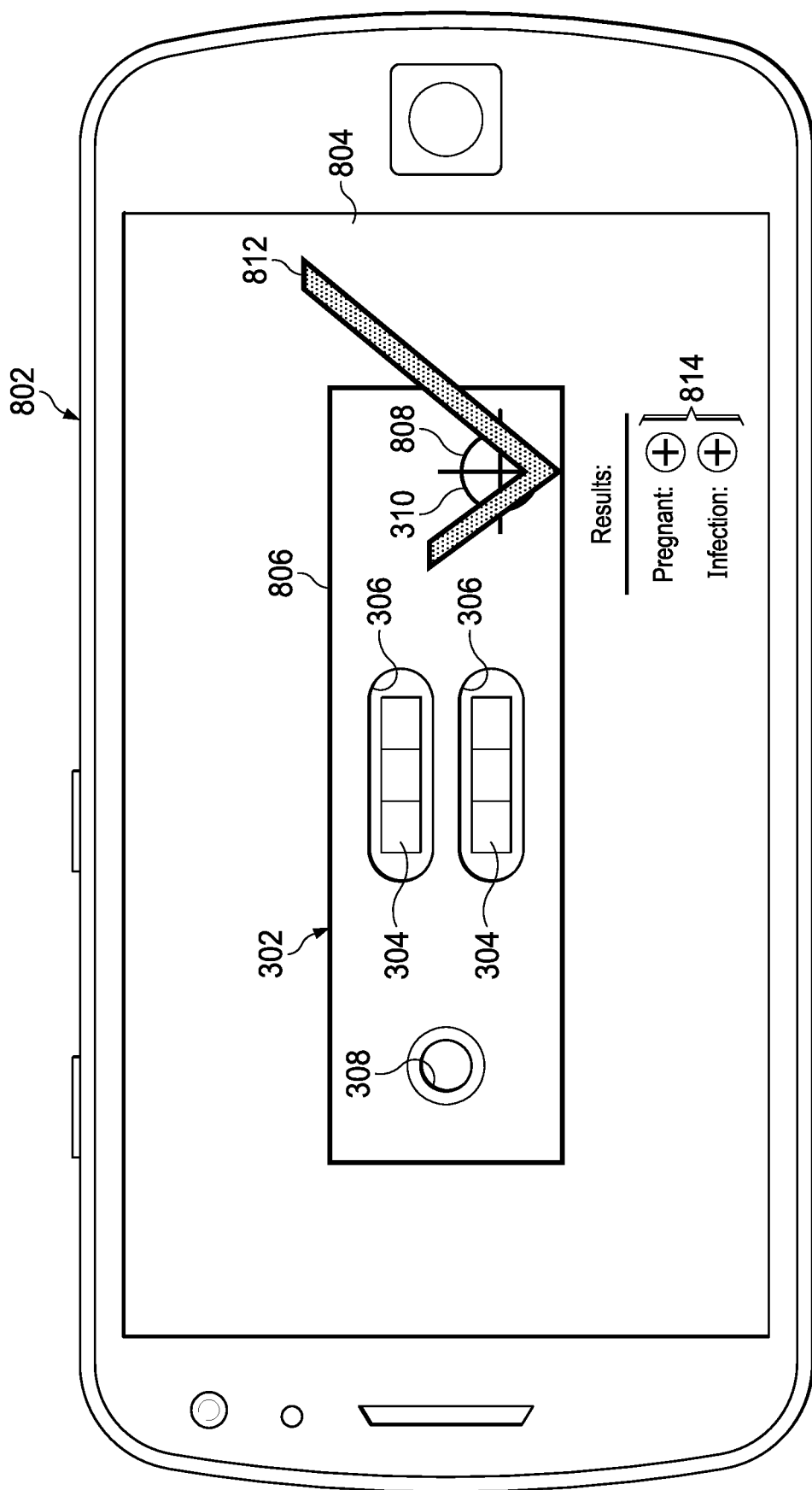
FIG. 8B illustrates a diagrammatic representation of one embodiment of a process for a mobile device application for testing device image capture and image processing, wherein an image alignment indicator is aligned with the subject of the image.

Referring now to FIGS. 8A and 8B, there is illustrated a diagrammatic view of one embodiment of a process 800 for a mobile device application for testing device image capture and image processing. The mobile device application allows for an image of a testing device, such as testing device 300, to be captured using a camera installed on a mobile device 802 having a screen 804. While the mobile device 802 displays on the screen 804 the scene captured by the camera, the mobile device application also displays a graphic on the screen 804 in the form of a boxed outline 806, the size of the outline 806 corresponding to the size of the testing device 300. Also displayed on the screen of the mobile device 802 within or near the outline is a crosshair graphic 808. A user of the mobile device 802 attempts to align the outline 806 with the borders of the testing device 300 and also attempts to align the crosshair graphic 808 with the crosshair 310 on the testing device 300. While alignment has not yet been achieved, a misalignment warning 810 may appear on the screen of the mobile device 802, indicating to the user that alignment has not yet been achieved. Such is shown in FIG. 8A.

In FIG. 8B, there is shown the result of a successful alignment of the outline 806 with the testing device 300 and successful alignment of the crosshair graphic 808 with the crosshair 310 on the testing device 300. As shown in FIG. 8B, once aligned, a success indicator 812 may appear, such as a check mark or other positive status symbol, on the aligned image. Successful alignment causes the camera on the mobile device 802 to capture the current image of the testing device 300. Other checks may occur, including ensuring that the image is focused before the image is saved. This image is then processed to determine a result based on the severity of the reaction occurring on the test strip. The mobile device application performs an analysis of the test line captured in the image, counting the number of colored pixels, as well as determining the intensity of the color. The mobile device may then compare this number and color intensity to that in the control line, providing a mathematical evaluation of the test line. Utilizing unique wavelengths of light for illumination in conjunction with either CMOS or CCD detection technology, a signal rich image is produced of the test lines to detect the colloid gold or latex particles. This provides an advantage because a user simply looking at the two lines may not know what the test line indicates, such as when the colored line does appears on the strip, but it is a faded line, rather than a dark line. Based on this analysis, the mobile device application may provide a results indicator 814.

The results indicator 814 may be a qualitative result or a quantitative result. For example, and as shown in FIG. 8B, a qualitative result for the results indicator 814 may indicate, in the case of a testing device for testing pregnancy as well as an infection, a plus sign next to a line reading "pregnant:" and a plus sign next to a line reading "infection:" to indicate that the user is both pregnant and infected with the bacteria or virus being tested, such as the Zika virus. For a quantitative result, the results might provide a numeric rating. For instance, a rating system between 1-100 may be used. If the results provide a low rating to the user, such as a rating of 10, this indicates a low risk of infection, although medical attention may be sought by the user anyway. For example, if the user is pregnant, and also receives a 10 rating for Zika, this may indicate that Zika was detected in low amounts. However, the user may still seek medical attention or further testing from her doctor because Zika has been known to cause birth defects. If the rating is a high rating, such as 95, this indicates that an infection has most likely occurred and medical attention should be sought immediately.

This same quantitative rating system may be applied to any test (viral infections, bacterial infections, pregnancy, and other health conditions), as the quantitative test can be performed using the software described herein to accurately test bound antibody concentrations on the test strip. In some embodiments, a combined qualitative and quantitative result may be presented, such as both a rating and a plus or minus sign being presented, or other types of quantitative and qualitative indications. Additionally, various combinations of tests may be provided for in the testing device, such as pregnancy/Zika, pregnancy/flu, pregnancy/strep/Zika, etc.

Figure 9:
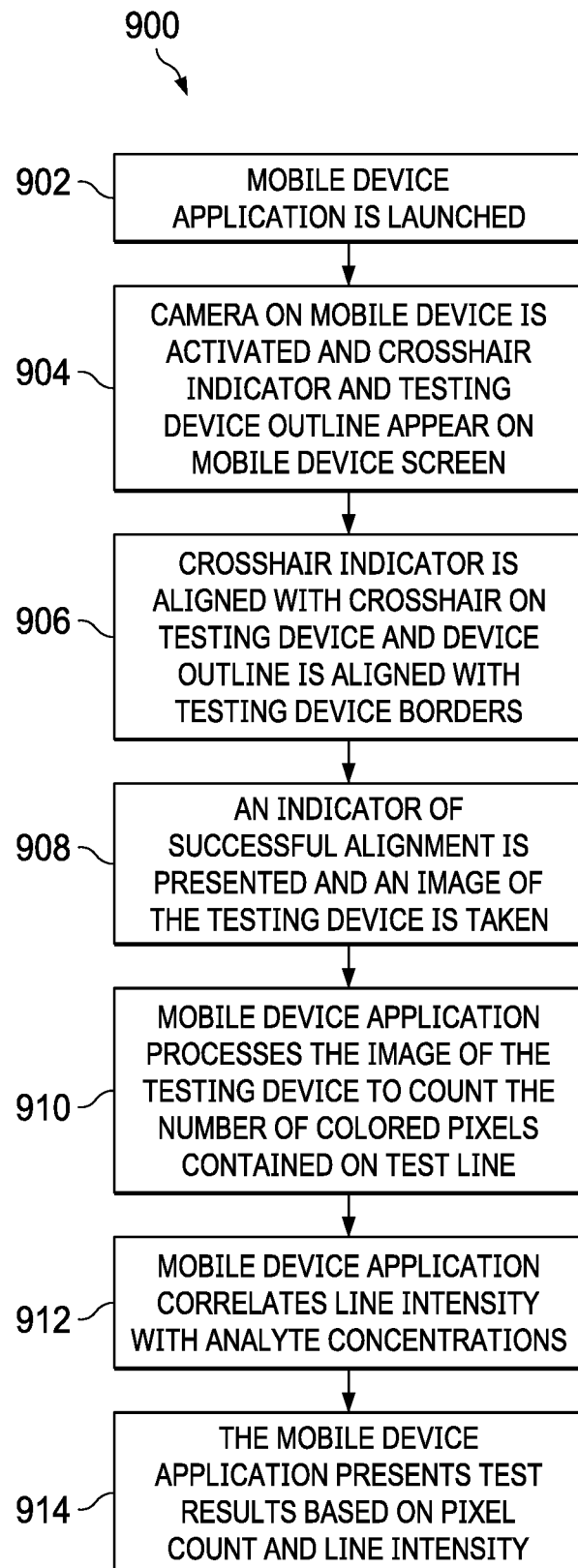
FIG. 9 illustrates a flowchart of one embodiment of an image analysis process using a mobile device.

Referring now to FIG. 9, there is illustrated a flowchart of one embodiment of an image analysis process 900 using a mobile device. At step 902 a mobile device application is launched. At step 904 a camera on the mobile device is activated and a crosshair indicator and a testing device outline appear on the mobile device screen. At step 906 the crosshair indicator presented on the screen of the mobile device is aligned with a crosshair icon on the testing device and the device outline presented on the screen of the mobile device is aligned with the borders of a testing device. At step 908, an indicator of successful alignment is presented on the screen and an image of the testing device is taken by the mobile device camera. At step 910, the mobile device application processes the image of the testing device to determine test line strength by counting the number of colored pixels contained in the test line. At step 912, the mobile device application correlates line intensity with analyte concentrations to further determine test line strength. At step 914, the mobile device application presents the test results based on pixel count and line intensity, providing either a qualitative or quantitative result.

In some embodiments, the number of pixels indicating bound antibodies on the strip may be measured against that in the control line to compare line intensity between the two lines, with the control line acting as an example of a strong reaction, indicating a strong infection, and determining how close the test line intensity is to the control line. This would lead to a logical quantitative result. For instance, if the test line is determined to have a pixel count and line intensity that is 25% of the pixel count and line intensity of the control line, a rating of 25 may be given. If a qualitative result is to be provided, a rating of 25 may give a qualitative result that is negative, or it could be positive depending on the type of condition being tested and known actual infection results where a rating of 25 occurred for that condition.

In some embodiments, the test line may not be compared with the control line to determine a result. Rather, the mobile device application may have access to a database having data on numerous past tests for the same condition. This data may instead be used as the control. This allows the application on the mobile device to retrieve data on past tests and compare the test line data of the current test to past tests. Overall data for past tests may be provided and compared against, such as providing an average or a curve of past tests, or individual tests rated as having accurate results may be compared against.

In addition to a status result of an infection or other medical condition being provided to the user, other indicators of health may also be tested and results thereon provided. This provides for potential early identification of pregnancy and risk of morbidity, allowing for medical attention to be sought much more quickly. Indicators of health may be detected from biologics, such as urine and blood. Urine, for example, allows for the detection of glucose levels, proteins, bacteria, and infectious markers. In the case of glucose, glucose is usually not found in urine, but, if it is, that is an indicator of extremely high levels of glucose in the body, where the kidneys release excess glucose into urine. This is often a sign of diabetes. Protein in the urine may indicate a malfunctioning of the kidneys, which could be the result of high blood pressure. Similarly, if blood is detected in urine, it could be a sign of a problem with the kidneys or the bladder. Blood, for example, allows for the detection of glucose, inflammation, hormones, genetic defect risks, and metabolic endocrine disorders.

Figure 10:
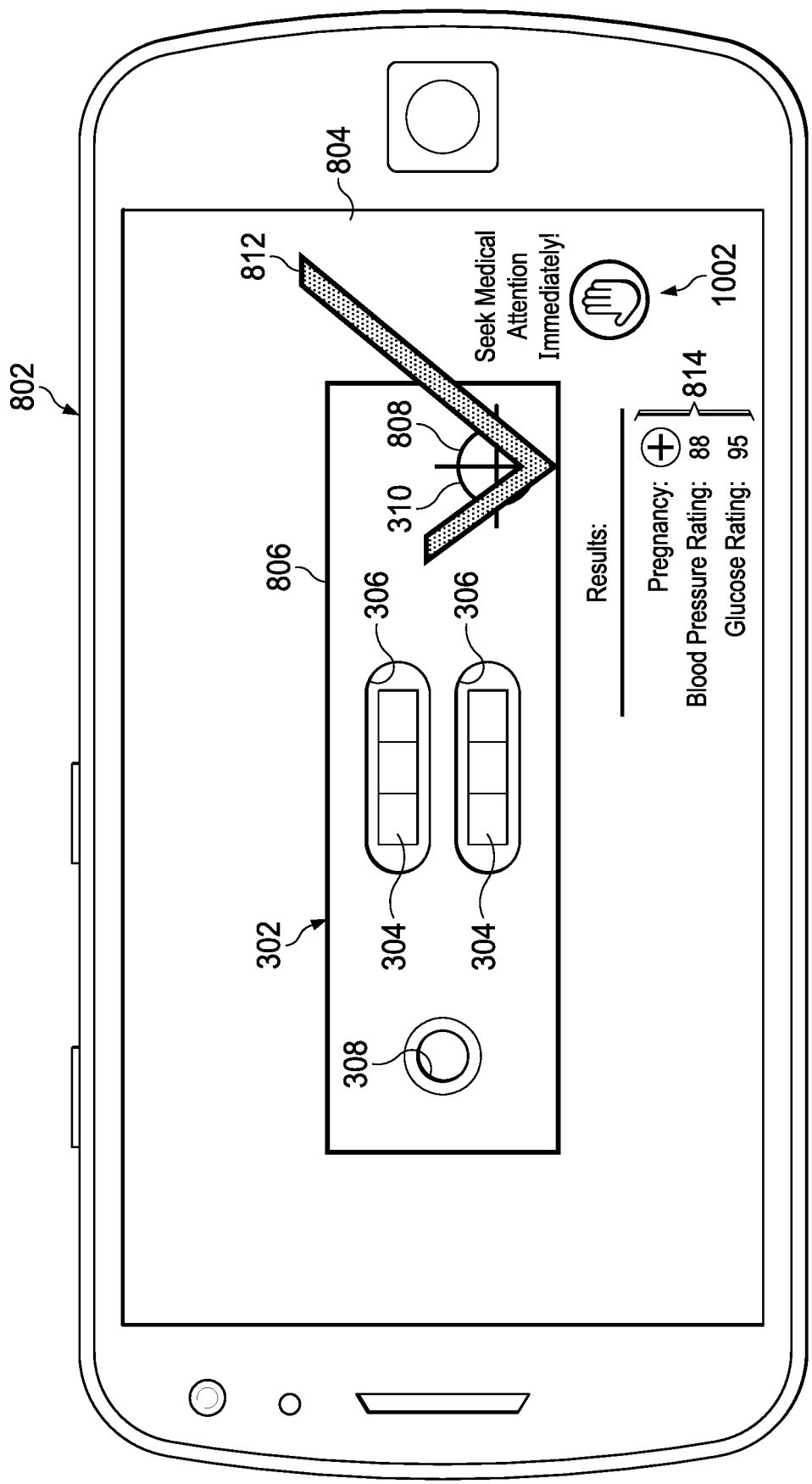
FIG. 10 illustrates a diagrammatic representation of another embodiment of a process for a mobile device application for testing device image capture and image processing, wherein an image alignment indicator is aligned with the subject of the image.

Referring now to FIG. 10, there is illustrated another embodiment of a successful alignment of the outline 806 with the testing device 300 and successful alignment of the crosshair graphic 808 with the crosshair 310 on the testing device 300, wherein quantitative results for health risk indicators are provided. In this embodiment, the results indicator 814 provides a qualitative result for pregnancy, and quantitative results for other health risk indicators. In the embodiment shown in FIG. 10, the health risk indicators being tested are markers for blood pressure and for glucose levels. For blood pressure, this is a test for markers in the blood that can be associated with high blood pressure. These could be test for such things as low levels of vitamin D and the such. Studies have shown that patients suffering from essential hypertension will be under oxidative stress and Malondialdehyde (MDA) is the principal and most studied product of polyunsaturated fatty acid pre-oxidation. This can show an indirect correlation with anti-oxidants, particularly with superoxide dismutases (SODs) (r=0.573) and catalase (r=0.633) representative anti-oxidant are involved in reducing the stress of a patient's biological system during hypertension. Another marker for hypertension is buildup of uric acid, where in uric acid is a marker for xanthine oxidase-associated oxidants and that the latter could be driving the hypertensive response. Additional markers are cortisol, a hormone. The test strips 604 can test for the different biological markers.

The results indicator 814 provides numeric ratings, in this case, 1-100, with the blood pressure rating being 88 and the glucose rating being 95. This indicates that both blood pressure and glucose are extremely high. Due to this, an additional alert indicator 1002 is presented to the user on the screen of the mobile device, alerting the user to seek medical attention immediately. This is to ensure that the health of both the pregnant woman and the fetus can be checked as close to the time of pregnancy detection as possible and medical attention received if needed.

Figure 11:
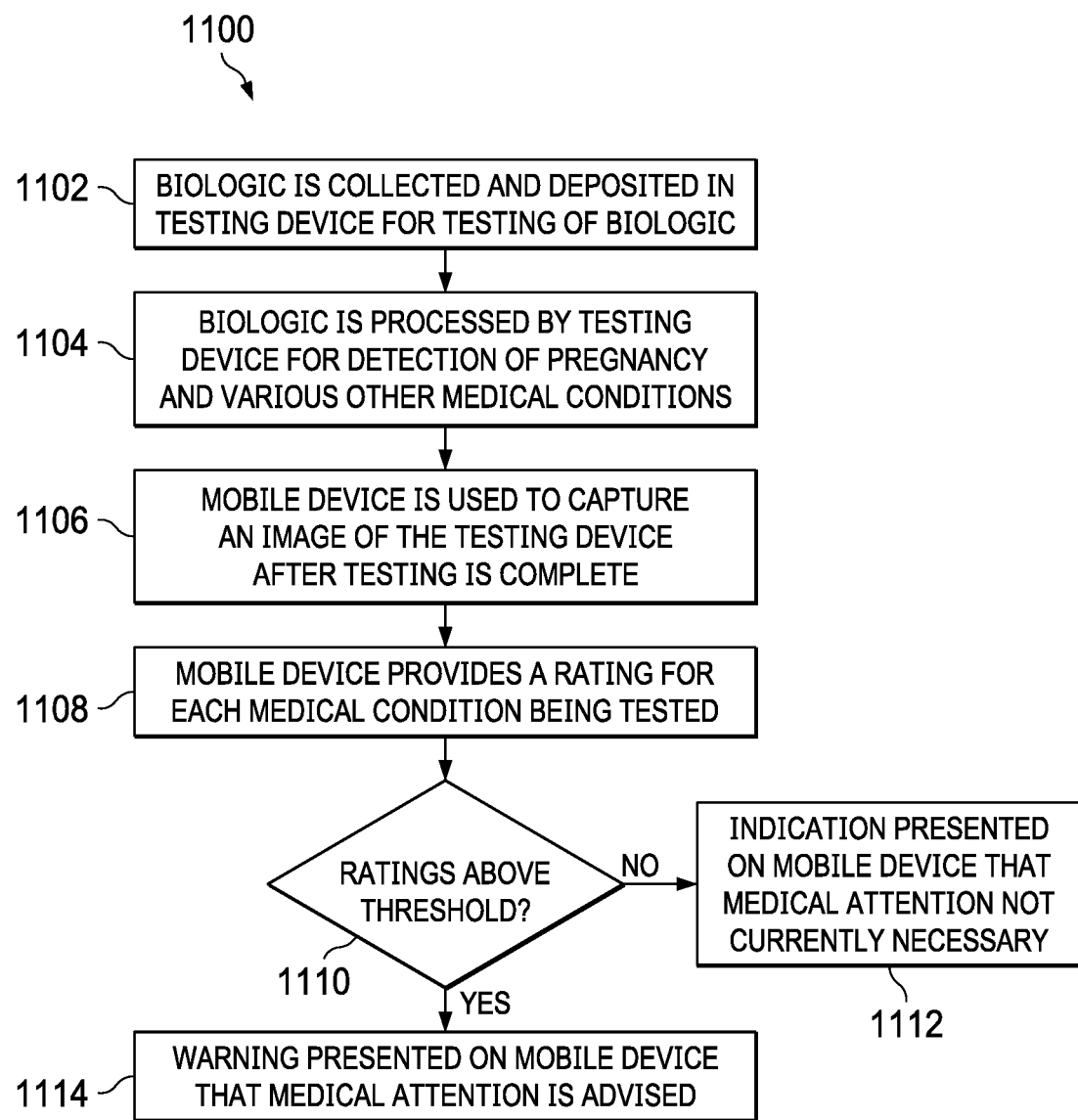
FIG. 11 illustrates one embodiment of a consumer driven biologic and disease data collection system.

Referring now to FIG. 11, there is provided a flowchart of one embodiment of a pregnancy disease risk assessment process 1100. The process 1100 begins at step 1102 where a biologic is collected and deposited in a testing device for testing of the biologic. At step 1104, the biologic is processed by the testing device for detection of pregnancy and various other medical conditions. These medical conditions may be high blood pressure, diabetes, bacterial or viral infections, inflammation, an increase in hormone levels, genetic disease markers, and/or metabolic disorders. At step 1106, a mobile device is used to capture an image of the testing device after testing is complete. In some embodiments, test results may be immediate. In other embodiments, and depending on the medical conditions being tested, the test may take a certain amount of time to complete. In this case, the user of the test would be alerted to this fact in instructions provided with the testing device. Additionally, a visual indicator on the testing device may alert the user that a test is now complete. At step 1108, the mobile device provides a rating for each medical condition being tested, such as that described with respect to FIG. 10 herein.

At decision block 1110, it is determined whether the ratings for each condition exceed a certain threshold for that condition. If not, the process 1100 moves to step 1112, where an indication is presented to the user via the mobile device screen that medical attention is not currently advised or necessary. If at step 1110 it is determined that at least one of the medical conditions being tested rises above a certain threshold, the process 1100 moves to step 1114 where a warning is presented to the user via the mobile device screen that medical attention is advised. The thresholds for medical conditions may not trigger a warning even if a rating exceeds a threshold, if, in the event of multiple tests being performed, the combined test results do not warrant immediate medical attention. For example, if a user is testing for a cold virus, blood pressure, and glucose, and only the cold virus rating is above the threshold, there may not be a warning provided to the user. Additionally, ratings may be weighted or aggregated based on the medical conditions being tested. For example, if blood pressure, inflammation, and glucose are being tested for, and they all are given only moderate ratings that do not rise above the threshold for any condition individually, an warning to seek medical attention may still be provided due to the combination of conditions taken together.

Figures 12, 13:
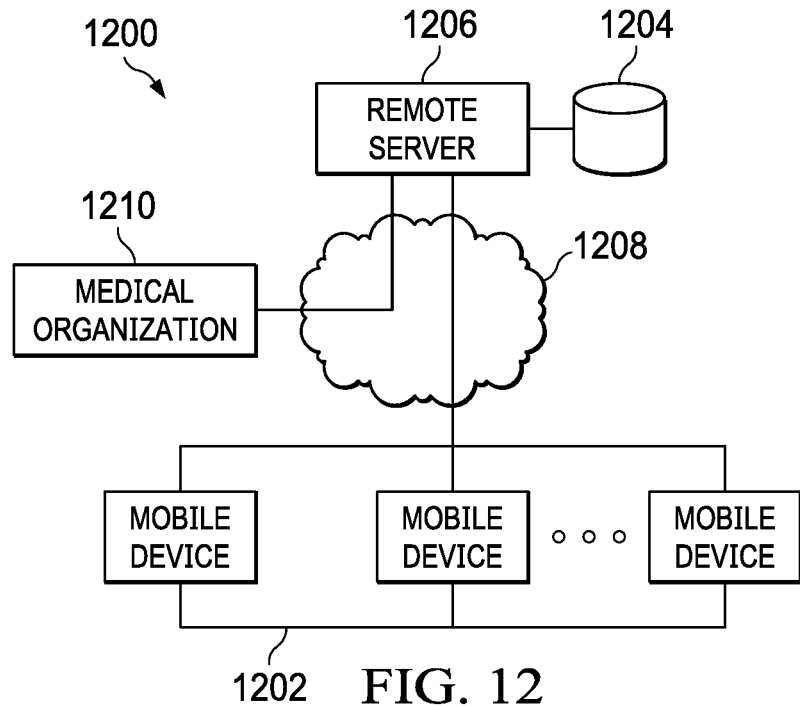
FIG. 12 illustrates one embodiment of a consumer driven biologic and disease data collection system.
FIG. 13 illustrates an example of a unique biologic ID database table.

Referring now to FIG. 12, there is illustrated one embodiment of a consumer driven biologic and disease data collection system 1200. Data collected from users performing the tests disclosed herein effectively can provide a wealth of information. As tests are performed data may be passed by a plurality of mobile devices 1202 being used by users performing tests to a database 1204, the database being at a remote server 1206, over a network 1208. The user is sourcing a biologic from user's own body. This is done at home, not in a lab, hospital, or clinic. Each particular test would expect a certain type of biologic to be provided. For instance, for a pregnancy test, a urine sample is provided and tested for pregnancy markers. For a stool test, the stool might be dissolved in a vial with a solution provided with the testing device/kit, and tested for various disease or infectious markers. Data and results from the tests may be stored on the database 1204 at the remote server 1206. As described herein, this data may be used as a control for testing analysis for users of the plurality of mobile devices 1202. This data may also be used to provide data sets for biologics to a medical organization 1210. The medical organization 1210 may be doctor's offices, researchers, hospitals, testing labs, and other individuals or organizations that have an interest in the health and analysis of users taking the test and of their biologic samples. In this way, data can be gathered from a variety of biologics tested for a variety of different medical conditions and characteristics.

Referring now to FIG. 13, there is illustrated an example of a unique biologic ID database table 1300. The table 1300 is illustrative of the type of data stored in association with data for a biologic transmitted by the plurality of mobile devices 1202 for storage on the database 1204. A biologic ID header 1302 is provided that shows that the biologic sample has been given a unique ID. All data concerning the biologic may be stored in association with the unique biologic ID. The table 1300 also includes a biologic type entry 1304. This designates what type of biologic that the biologic associated with the unique ID is, such as blood, urine, stool, saliva, sweat, or other biologics. The table 1300 also provides a plurality of test ratings 1304, for various tests performed on the biologic. In the example shown in FIG. 13, a blood biologic is provided having an assigned ID of 2402, and having been testing for pregnancy markers, the Zika virus, and for glucose levels. The rating for pregnancy was a 99 rating, the rating for a Zika infection was a 75, and the rating for glucose levels was a 10. This would indicate that the test subject has an extremely high likelihood of both a pregnancy and a Zika infection, which would have resulted in a warning to seek medical attention at the conclusion of the tests. Other information may also be stored in the database in relation to the biologic, including other condition ratings, time and date each test was performed, user information such as ethnicity, gender, and age, and status indicators such as whether a test subject visited a physician as a result of the tests. The database 1204 thus provides the test subject with a growing collection of information that may be accessed by the test subject. This allows the test subject to present the test results to her physician for medical attention or additional testing, and allows for others who may access the database, such as disease researchers, to have access to data on various biologic samples and their markers.

Figure 14:
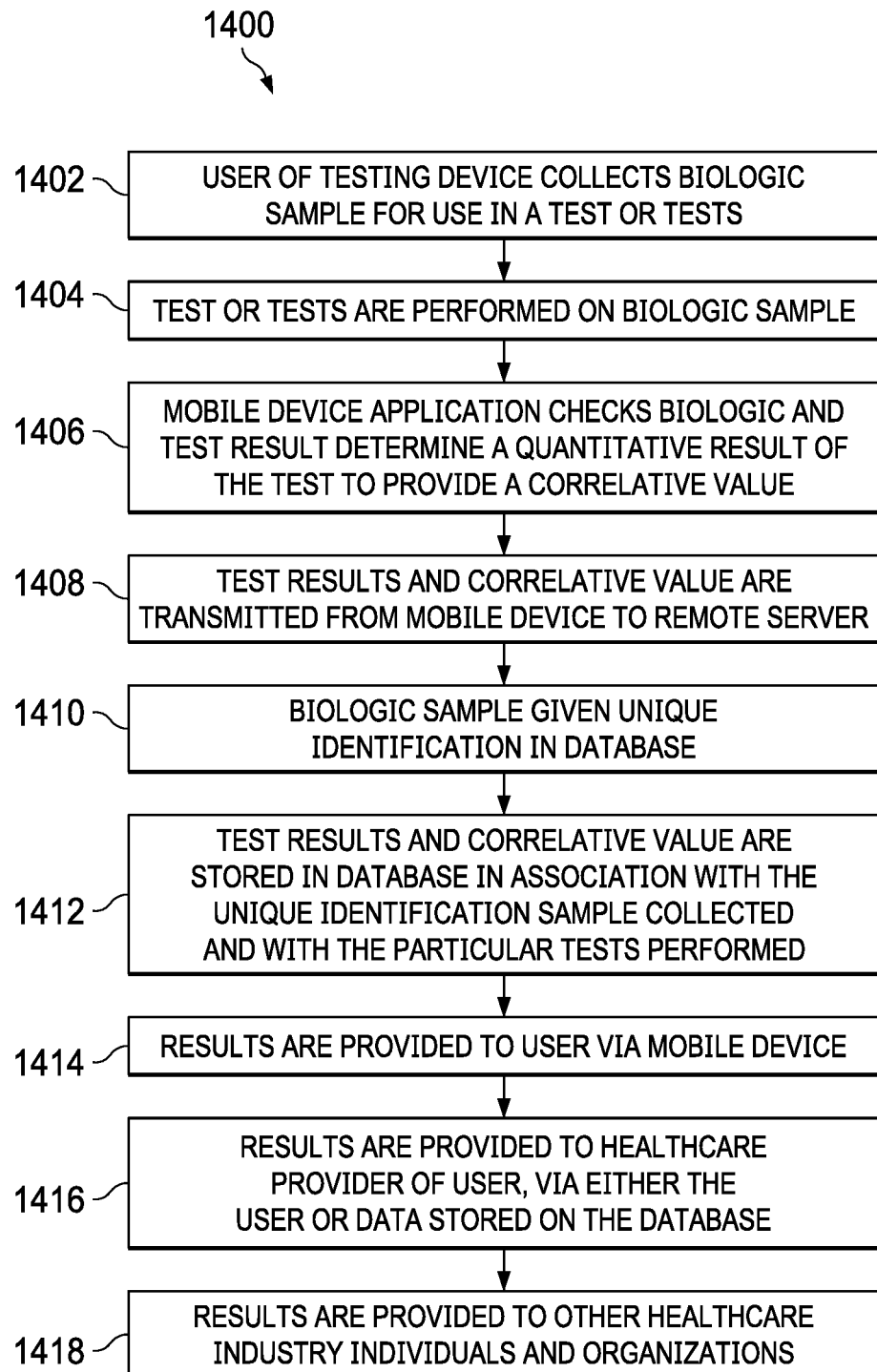
FIG. 14 illustrates a flowchart of one embodiment of a biologic data collection and dissemination process.

Referring now to FIG. 14, there is illustrated a flowchart of one embodiment of a biologic data collection and dissemination process 1400. The process 1400 begins at step 1402 where a user of a testing device collects a biologic sample for use in a test or a series of tests. At step 1404, the test or series of tests are performed on the biologic sample. At step 1406, a mobile device application checks the biologic sample the testing device result to determine a quantitative result of the test to provide a correlative value for the condition being tested in the biologic sample. At step 1408, the test results and correlative values, or multiple values if multiple tests on the biologic sample were conducted, are transmitted to the remote server 1206. At step 1410, the biologic sample is given a unique identification number in the database 1204. At step 1412, the test results and correlative value or values are stored in the database 1204 in association with the unique identification number given to the biologic sample collected and in association with the particular tests performed. This way, the particular biologic sample may have various characteristics stored and retrieved in association with the biologic sample, and the test results may also be retrieved when data on a particular test is needed on a cross-section of users.

At step 1414, the results are provided to the user on the user's mobile device. At step 1416, the results are provided to the user's healthcare provider. The healthcare provider may receive the test results due to a visit from the user, the user bringing the results of the test with her on her mobile device, or the healthcare provider may receive the results from the database 1204 if the healthcare provider has permission to access the database 1204, or if access is granted in anticipation of the user's appointment with the healthcare provider. At step 1418, the test results are also provided to other healthcare industry individuals and organizations, including medical researchers, hospitals, and others.

Figure 15:
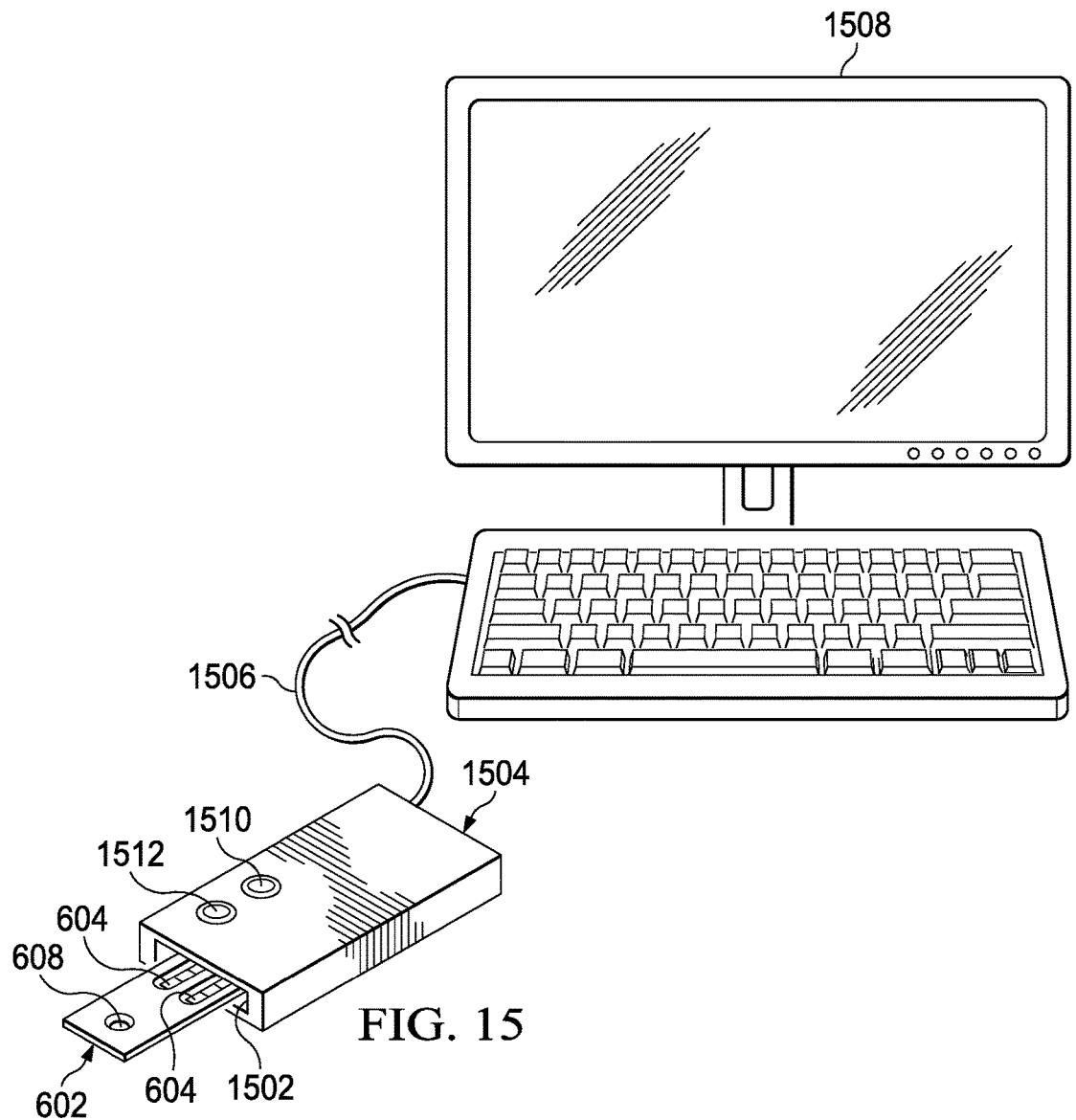
FIG. 15 illustrates a perspective view of a system for scanning test strips.

Referring now to FIG. 15, there is illustrated a perspective view of a system for scanning test strips. The housing 604, as described hereinabove with respect to FIG. 6, is illustrated as being disposed within a slot 1502 in a test housing 1504. The test housing 1504 is connected through a line 1506 to a PC 1508. When the housing 604 containing the test strips 604 after being subjected to the biologics is inserted within the slot 1502, the test housing 1504 will scan the test strips 604 and analyze the results with the PC 1508. The PC 1508 will run some type of algorithm that can analyze the results of both of the test strips 604. There can be provided to indicators 1510 and 1512 on the surface of the test housing 1504, one being, for example, a ready LED and one being a green LED. The PC 1508, after analyzing results, can then provide a warning indicator such as lighting up the green LED for a positive indication of pregnancy and the red LED for indicating that there is some issue. As an example, suppose that the second test strip tested for the Zika virus. If so, a warning would be appropriate to output and activate the red LED. There could be any other type of indicator associated with the second test at 604 that, in a combination with the test results of the first test strip, i.e. for testing for the presence of a pregnancy state, testing for such things as diabetes, etc. Further, although only two test strips 604 are illustrated, there could be multiple test strips testing for many different biological issues that may be present in an individual. In this embodiment, by inserting the housing 602 into the test housing 1504 and allowing the PC 1508 to analyze the results, the indicators associated with the test strips can be analyzed with the assumption that all of the test return results were associated with an individual and in proximate time to each other. That means that the individual patient applied biological specimens, such as urine, blood, etc., to the appropriate test strips and, since these were all contained within the same test strip housing 602, this provides an indication that they are associated with a single patient. Further, the test performed will typically be a test that will provide a very short-term response. Thus, the specimens can be applied to the test strips 604 in the test strip housing 602 and then inserted within the slot 1502 for testing by the PC 1508.

Figure 16:
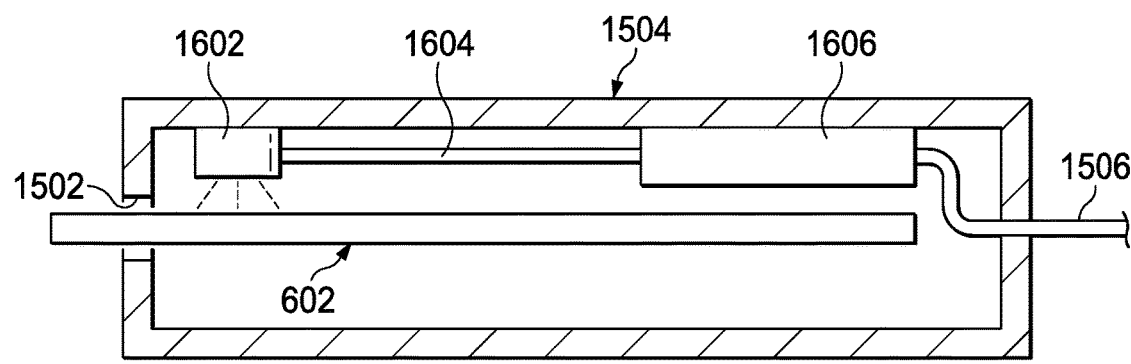
FIG. 16 illustrates a cross-sectional view of the system of FIG. 15.

Referring now to FIG. 16, there is illustrated a cross-section of the test housing 1504. It can be seen that the test strip housing 1602 is passed in slot 1502 past the camera 1602. The camera 1602 is operable to scan a small cross-section of the test strips 604 on the surface thereof as the test strip housing 602 passes thereby. Of course, there could also be a much larger camera provided for taking an entire image of the test strips 604 after being inserted within the test housing 1504. The camera 1602 is connected via a wire 1604 two in electronics package 1606 to process the information and send it to the PC 1508. The electronics package 1606 will also drive the indicators 1510 and 1512.

Figure 17:
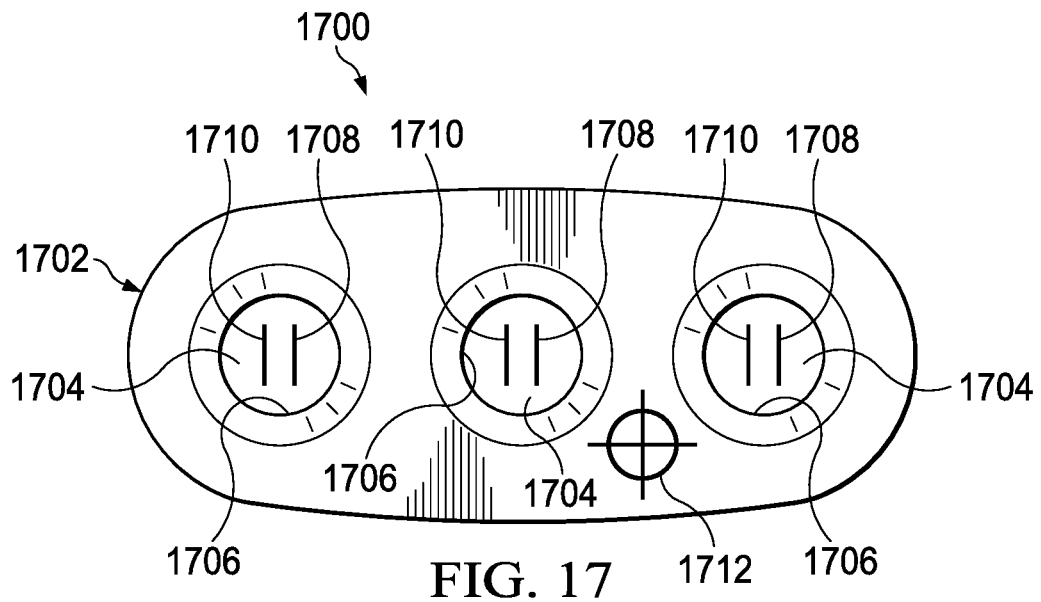
FIG. 17 illustrates one embodiment of a vertical flow immunoassay device.

Referring now to FIG. 17, there is illustrated one embodiment of a vertical flow immunoassay device 1700. It will be understood that testing device 300 and other embodiments herein illustrate a lateral flow immunoassay device. However, other types of immunoassay devices may be used. For example, vertical flow immunoassay devices may be used, a two-sided flow through assay, or even a sandwich ELISA test may be run.

The testing device 1700 includes a housing 1702 that forms the body of the testing device. The housing 1702 may be made of plastic, metal, or any material durable enough for shipping and subsequent handling by a user. The housing 1702 may be hollow so that a plurality of immunoassay test pads 1704 may be housed within and so that a biologic may be deposited within the housing 1702. The testing device 1700 may further have a plurality of sample wells 1706, each sample well having one of the plurality of immunoassay test pads 1704 disposed within, and allowing for a user to view at least a section of a nitrocellulose membrane of each of the immunoassay test pads 1704, the membrane 1708 having a test line 1708 and control line 1710. The testing device 1700 may also have disposed on the surface of the housing a crosshair symbol 1712, used as an alignment target. This symbol may be a graphic printed or adhered to the testing device 1700. The crosshair symbol 1712 is used to align the testing device 1700 for the taking of an image of the testing device 1700 using a camera on a mobile device, for use in a mobile device application described herein. In other embodiments, the crosshair symbol 1712 may be other types of symbols, such as a simple shape (circle, square, etc.), other images (such as a medical cross symbol, an arrow, etc.), or any other type of image. In other embodiments, the device 1700 may be configured in such a way as to allow a biologic sample to be deposited into a sample well, and to present the results of the test on the opposite side of the housing. Such a configuration would allow the biologic to flow through the testing pad within the housing, with the reaction occurring on a reactive membrane on the side of the device opposite the sample well, with the device having a window for viewing the results.

Figure 18:
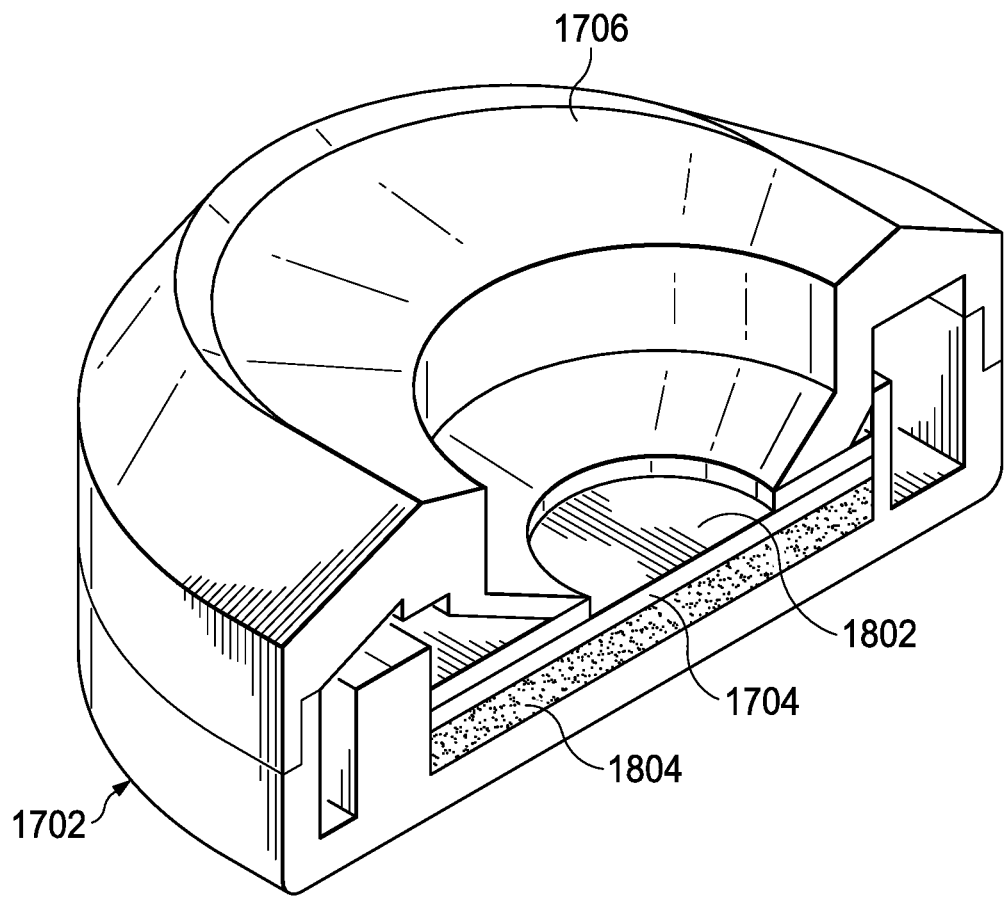
FIG. 18 illustrates a cross-sectional view of one embodiment of the vertical immunoassay device of FIG. 17.

Referring now to FIG. 18, there is illustrated a cross-sectional view of one embodiment of the vertical immunoassay device 1700. There is shown one of the plurality of immunoassay test pads 1704 residing within the housing 1702 below one of the plurality of sample wells 1706. The one of the plurality of immunoassay test pads 1704 includes a immunoreactive membrane 1802, such as the nitrocellulose membranes disclosed herein. The immunoreactive membrane 1802 may have particle conjugates disposed thereon that binds when a biologic sample is received onto the immunoreactive membrane 1802 via the sample well 1706, if the biologic sample contains the antigens or antibodies, or other indicators, for which the test is configured. The one of the plurality of immunoassay test pads 1704 also includes an absorbent pad 1804 for collection of excess biologic sample. It will be understood that the cross-sectional view illustrated in FIG. 18 shows one well of the plurality of sample wells 1704. The other wells included in the device 1700 would be configured in a similar manner as that shown in FIG. 18. There may also be included in the device 1700 an inner separating wall between each of the plurality of immunoassay test pads 1704, to ensure that excess biologic material that is not adequately absorbed by the absorbent pad 1804 does not contaminate neighboring immunoassay test pads.

Figure 19:
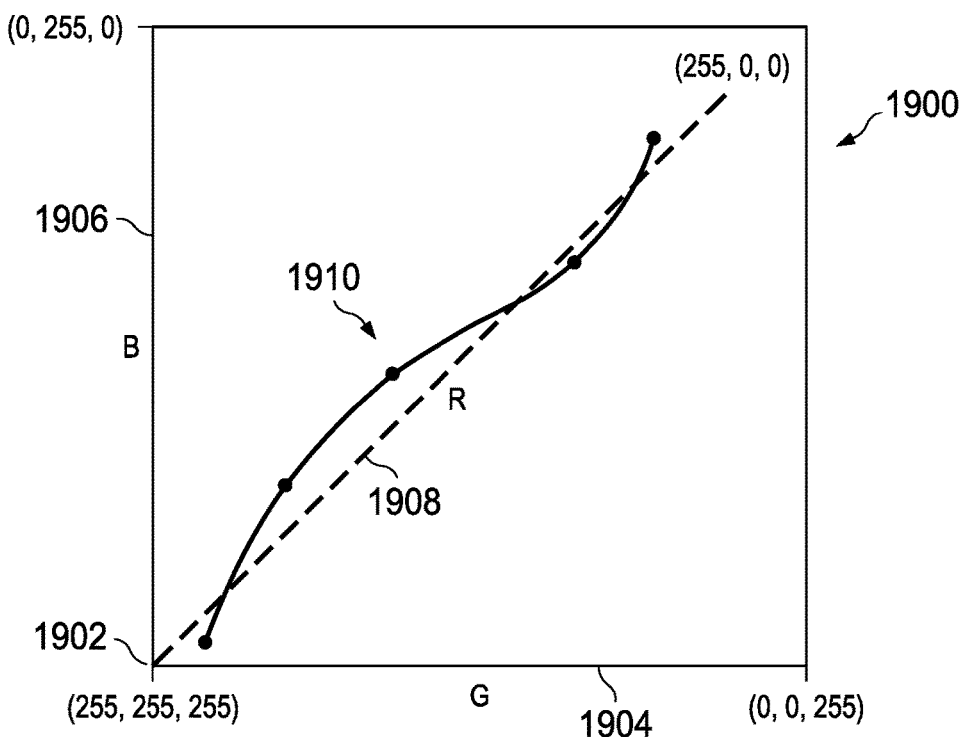
FIG. 19 illustrates a color gradient chart.

Referring now to FIG. 19, there is illustrated a color gradient chart 1900. When the mobile application described herein captures an image of the testing device, in some embodiments each pixel that makes up the test line captured in the image is processed to place it on a color gradient scale. In some embodiments, this placement may be done by examining the RGB values of the pixel. For any given test, there may be a visual color indicator (such as a test line) presented to the user of the test to indicate whether a reaction occurred. The color that is to be presented is known for the given test. Additionally, in some embodiments, the strength of the reaction will affect the strength of the color indicator. For example, if a test is supposed to produce a brown colored indicator, an image can be taken of the colored indicator to examine each pixel of the colored indicator to determine the strength of the color produced on the testing device, which indicates the strength of the reaction, and thus the risk level for the user.

The embodiment illustrated in FIG. 19 uses as an example a set of pixel RGB results for a test that produces a red colored indicator on the test strip when a reaction has occurred. There can be seen an origin point 1902 on the chart 1900, wherein the RGB value is (255, 255, 255) or white. This may represent a no reaction state for the test strip, since the test line on the strip may only appear as a white blank space if no reaction has occurred. An x axis 1904 represents the color green, wherein the amount of green in the pixel decreases as it moves away from the origin in relation to the x axis 1904. A y axis 1906 represents the color blue, wherein the amount of blue in the pixel decreases as it moves away from the origin in relation to the y axis 1906. A diagonal line 1908 running in between the x axis 1904 and the y axis 1906 represents the color red, wherein the diagonal line 1908 running through the center of the chart 1900 is a maximum red color all along the diagonal line 1908. If a pixel has less red than a 255 value, the pixel would be plotted away from the diagonal line 1908 in relation to whichever color is more predominant. For instance, if the pixel has RGB values of (127, 50, 205), a shade of purple, the pixel would be plotted somewhere in the lower right quadrant of the chart 1900. FIG. 19 further illustrates an example plurality of pixel plot points 1910, connected by a curved line, wherein the example plurality of pixel plot points 1910 shows tests results that likely indicate a positive reaction, as the plot points are all located near the diagonal line 1908, demonstrating that the colored indicator was a heavy red color for the most part.

Figure 20:
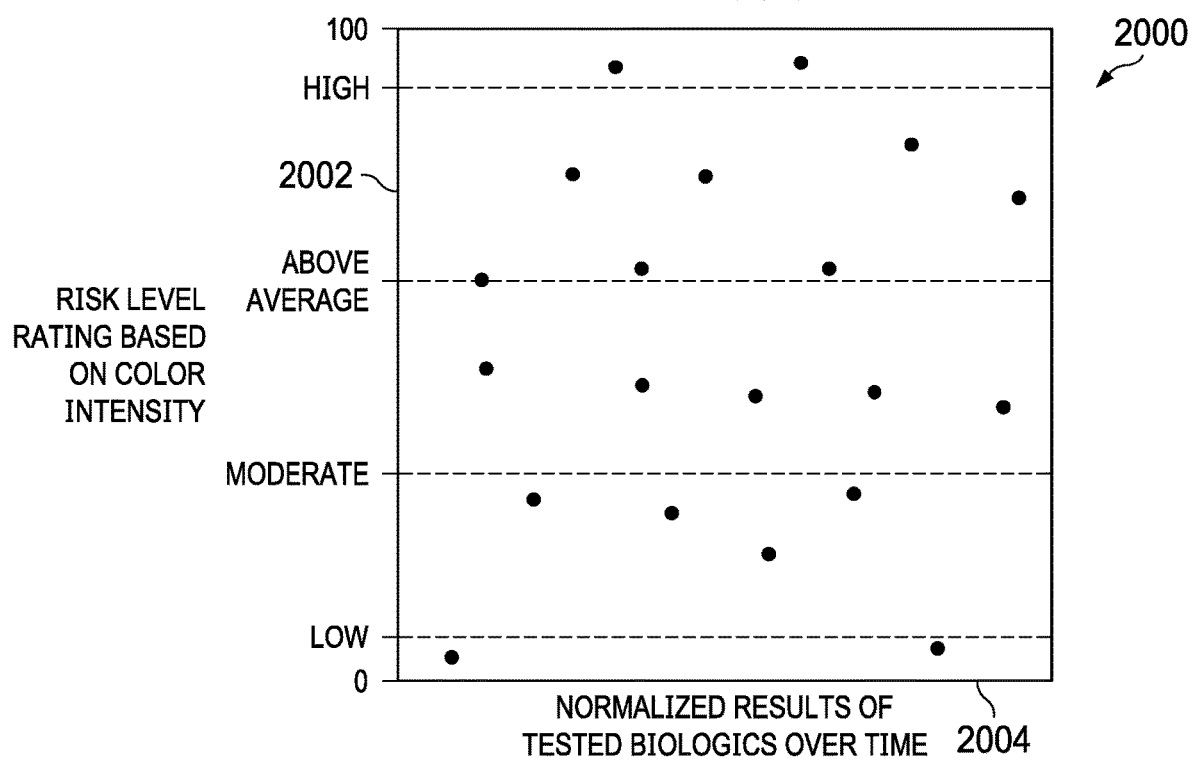
FIG. 20 illustrates a normalized past tests results rating chart.

Referring now to FIG. 20, there is illustrated a normalized past tests results chart 2000. The captured pixels may be normalized into a single value for determining whether there is a likelihood of infection, pregnancy, or whatever else the test is designed to detect. This may be done in various ways. For example, the shade of red in all the pixels may be averaged to reach a single RGB value. Outliers may be left out so that the average is not heavily skewed, especially when there are few outliers present. This RGB value may then be given a value, such as a risk rating, ranging from 0 to 100. For example, an RGB value of (255, 255, 255) would be given a rating of 0. An RGB value of (255, 0, 0) would be given a rating of 100. An RGB value of (205, 150, 75) may be given a rating of 70, and so on. This normalized value may then be used to compare the user of the test to users of past tests to determine a risk level. In some embodiments, the control line and the test line may be captured and the results compared, as well. In addition, the real results of risk levels may also be used to adjust the stored normalized value. For instance, if a particular RGB value that seems to indicate a strong reaction repeatedly was found to not indicate an infection, this value may be adjusted to provide a lower risk rating. For instance, if a physician who saw a patient who had a (205, 150, 75) RGB value later reported to the operator of the server 1206 that further testing showed no infection was present, and if this trend continued substantially as reported by other physicians or medical organizations, subsequent test results by other test users that were near the RGB value of (205, 150, 75) may be given a lower rating.

Chart 2000 illustrates how past tests results may be collected and used to determine the risk of a current test user. A y axis 2002 represents a risk level rating, ranging from 0 at the origin to 100. An x axis 2004 represents time, wherein a plurality of normalized test results is plotted on the chart 2000. The chart 2000 is further divided into sections across the y axis 2002, indicating various risk level thresholds. For instance, and as illustrated in the chart 2000, there may be at certain rating levels different thresholds of risk labeled as low, moderate, above average, and high risk levels. These thresholds may be moved over time as more data is accumulated via users conducting tests and the mobile application storing the data on the tests. When a user conducts a test, the user's normalized rating can be plotted similarly to past test results and weighed against them in order to provide a risk level for the user.

Figure 21:
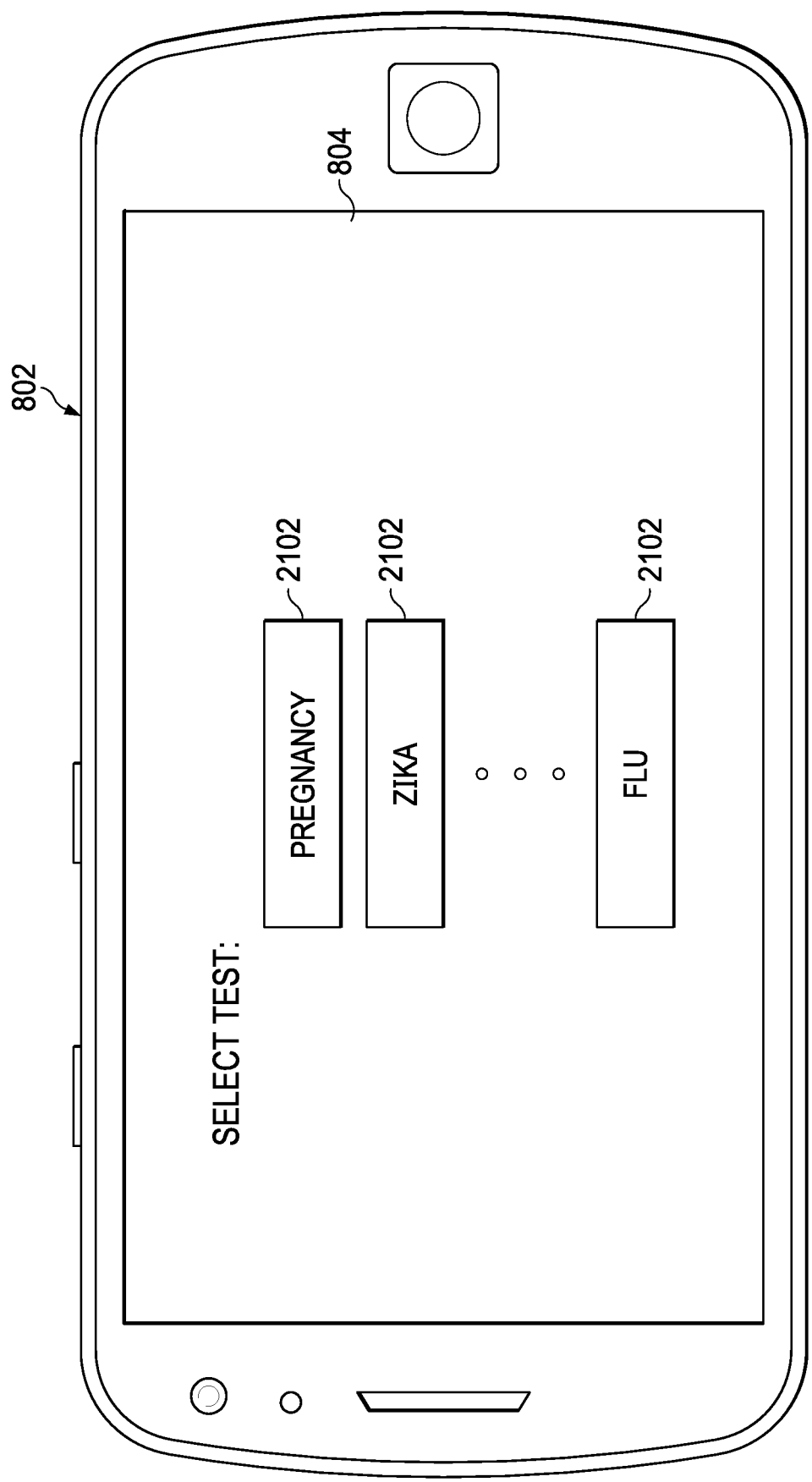
FIG. 21 illustrates a mobile device displaying on a screen a mobile application variable test functionality.

Referring now to FIG. 21, there is illustrated the mobile device 802 displaying on the screen 804 a mobile application variable test functionality. There is displayed on the screen 804 a plurality of test functions 2102. The plurality of test functions 2102 may be buttons that can be selected by a user to switch between tests within the mobile application. This allows for all test functions to be within the same mobile application. For each test run by the mobile application, data for the particular test chosen is utilized in performing the test, pulling the data from the remote server 1206.

Figure 22:
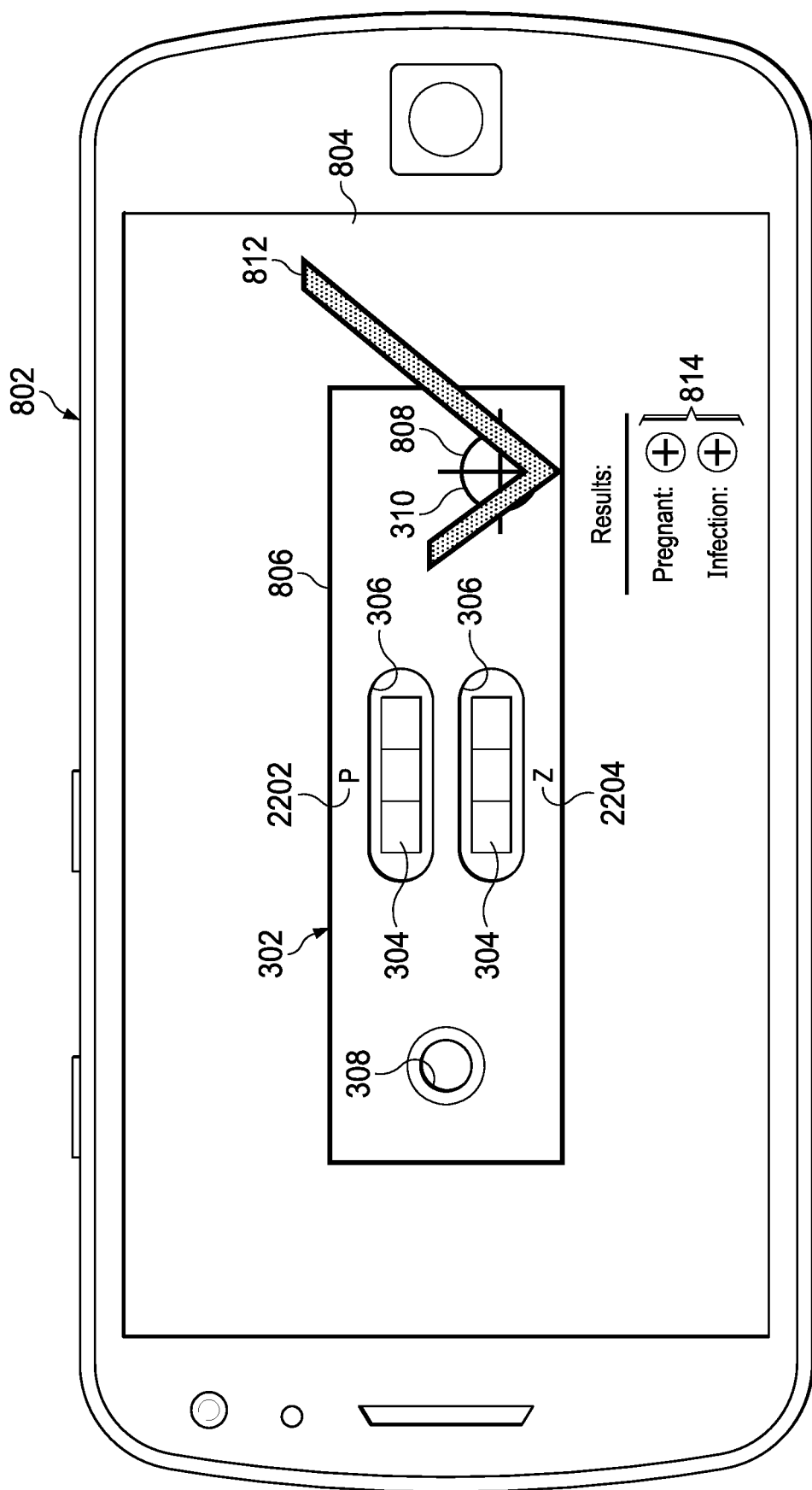
FIG. 22 illustrates the mobile device of FIG. 21, wherein a housing of a testing device also includes thereon test function indicators.

Referring now to FIG. 22, there is illustrated the mobile device 802 of FIG. 8B, wherein the housing 302 of the testing device 300 also includes thereon test function indicators 2202 and 2204. The test function indicators 2202 and 2204 are visual markers located on the housing 302 that identify to the mobile application the types of tests for which the testing device 300 is configured. These indicators may be any symbol, alphanumeric character, shape, etc. that can be added to the surface of the testing device 300. The mobile application is programmed to recognize the indicator and perform the test function associated with the indicator. For example, the embodiment illustrated in FIG. 22 shows a "P" symbol for test function indicator 2202 and a "Z" symbol for test function indicator 2204. In this embodiment, test function indicator 2202 indicates that one test strip in the testing device 300 is a pregnancy test, while test function indicator 2204 indicates that one test strip in the testing device 300 is a Zika test. This is used for merely illustrative purposes, and any recognizable symbol may be used for these two test functions, and any other type of test may have a symbol assigned in this way as well. Further, in some embodiments there may only be one indicator on the housing 302, even if there are multiple tests. This single indicator would be for the combined test. For example, if the testing device 300 of FIG. 22 had a single symbol of "PZ," this would indicate that the testing device 300 is a combined pregnancy and Zika testing device, allowing for the mobile application to recognize such and perform each test with knowledge of which strip is associated with each test based on the stored data on the testing device associated with the "PZ" symbol.

Figure 23:
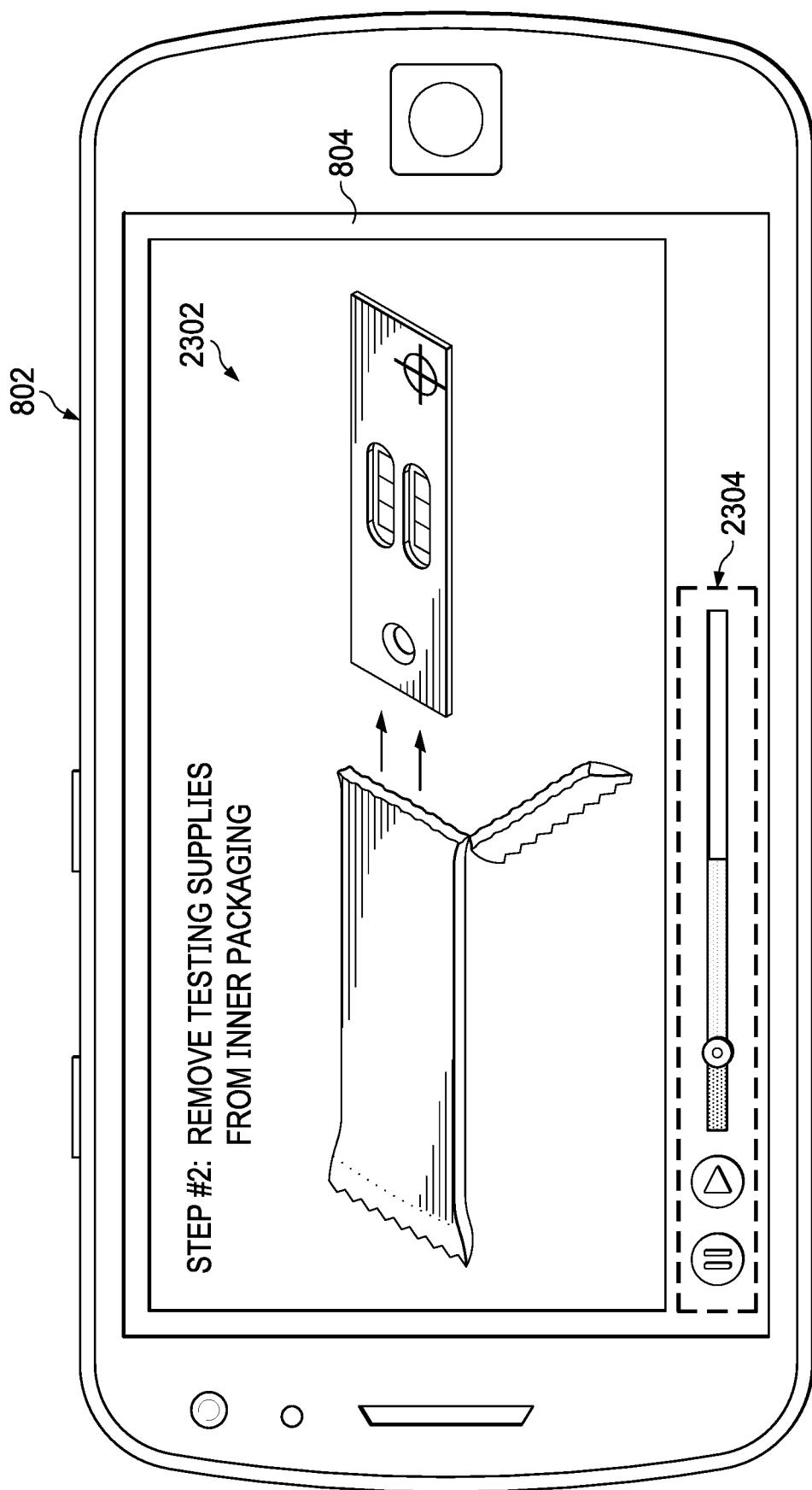
FIG. 23 illustrates a mobile device displaying audiovisual instructions for performing a self-diagnostic test.

Referring now to FIG. 23, there is illustrated the mobile device 802, which in some embodiments is also used to provide users instructions on how to perform a self-diagnostic test. It is important for users to be able to use diagnostic test products correctly in order to obtain the most accurate results and to avoid possible injury to his or herself. Tests that require a blood sample for the biologic, for example, might require the user to prick his finger to obtain the blood. A user could cause injury to himself if this is not performed correctly. Or, providing the wrong type of biologic, saliva instead of urine, for example, to the sample well 308 or a test strip 100 would likely cause inaccurate results. For these types of reasons, it is important for the user to be able to perform the test properly. Various regulations also require that the users of self-diagnostic tests be sufficiently instructed on the proper use of the tests and testing procedures. In some embodiments, such as is illustrated in FIG. 23, instructions for collecting performing the diagnostic test are provided by the mobile application in video and/or audio form. Before collecting the biologic and performing the diagnostic test, the user launches the mobile application on the mobile device 802. The mobile application then provides the user with step-by-step instructions for the test. In the embodiment illustrated in FIG. 23, a set of video instructions 2302 is presented on the screen 804. The video instructions 2302 give detailed guidance on how to collect the biologic sample or samples and how to put the samples into the testing device 300, as well as any other steps necessary for the test. In some embodiments, the mobile application includes controls 2304 which allow the user to play, pause, or replay the video instructions 2302 or parts of the video instructions. In some embodiments, the instructions for the diagnostic test are delivered by the mobile application on the mobile device 802 in an audio format. In these embodiments, the mobile application will still show various controls 2304 on the screen 804 which allow the user to play, pause, or replay the audio instructions.

In some embodiments, the file for the video or audio instructions are stored on the mobile device 802, while in other embodiments, the files are stored on remote servers and then downloaded or streamed to the mobile device when the user wishes to view/listen to the instructions.

Figure 24:
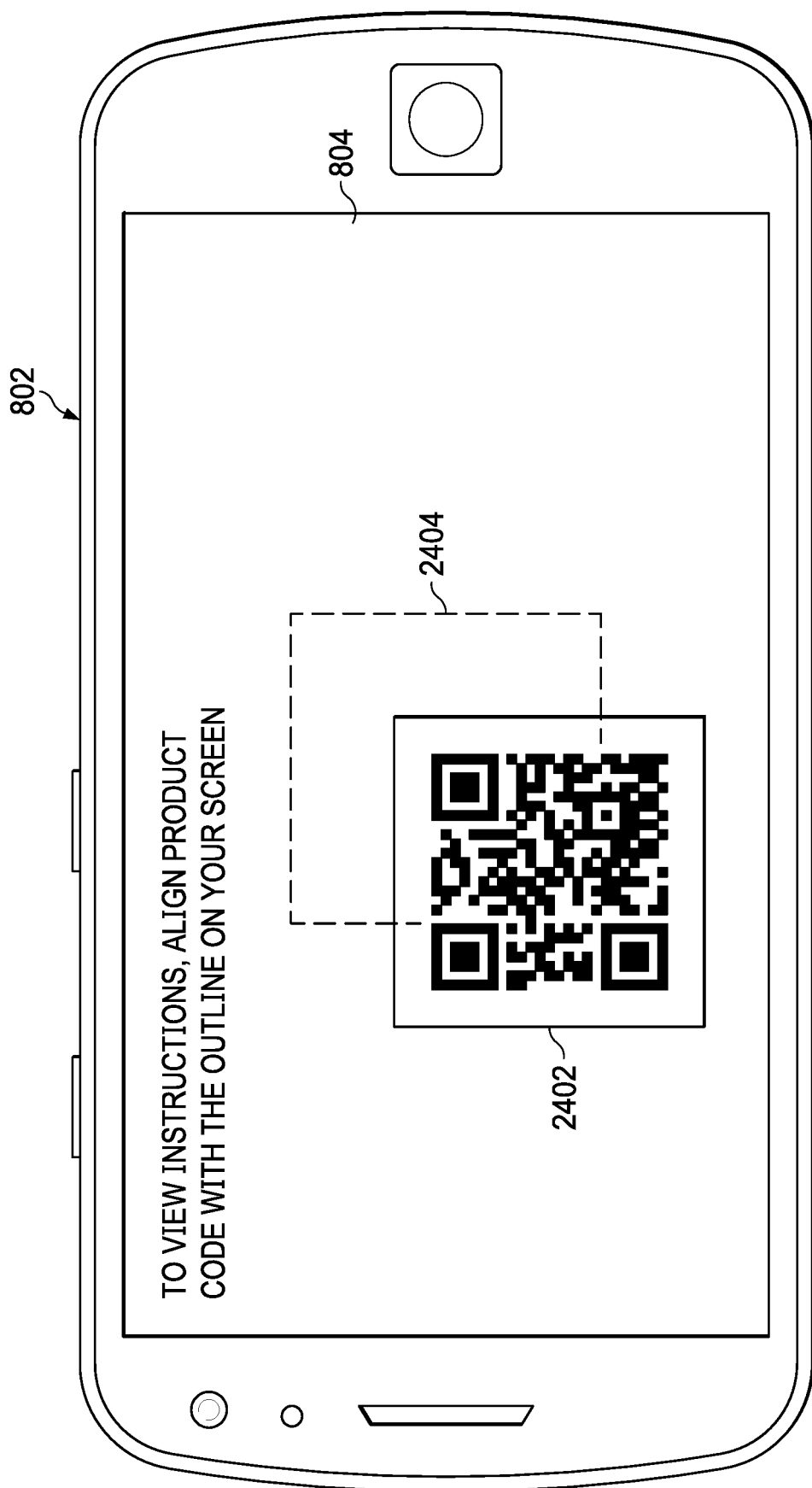
FIG. 24 illustrates a process for using a mobile device camera to capture an image of a scan-able code to determine which set of instructions is correct for a self-diagnostic test.

Turning now to FIG. 24, there is illustrated an embodiment in which a mobile device 802 running the mobile application allows users to access test instructions by scanning a computer-readable code. In these embodiments, which allow users to receive instructions via video or audio formats as described hereinabove with respect to FIG. 23, initiation of the instructions arises from scanning a code with the camera of the mobile device 802. The mobile application allows for an image of a scan-able product code 2402, which could be a bar code, a QR code, an alphanumeric code, or any other image than can be decoded by the application's software, to be captured by a camera on the mobile device 802. The scan-able product code 2402 may be found on the exterior packaging of the product, on documentation included with the product, or even on some component of the self-diagnostic test product itself. The scan-able product code 2402 is linked to the particular type of self-diagnostic test with which the code was included. This allows the application software to determine which set of instructions need to be presented to the user. Similar to the testing device image capturing and image processing described hereinabove with respect to FIGS. 8A and 8B, the application displays a graphic 2404 which helps the user align the scan-able product code 2402 in the field of view of the mobile device 802 camera so that the camera can capture an acceptable image. When the scan-able product code 2402 aligns with the displayed graphic 2404, the mobile application software recognizes this condition and captures an image of the product code. The mobile application then processes the image of the scan-able product code 2402 and accesses a database to find which set of instructions need to be presented to the user. In some embodiments, this database is stored in the software on the mobile device 802, while in other embodiments, the database is stored on a remote server and is accessed by the mobile device through the internet. Once the mobile application has determined from the database which set of instructions need to be presented to the user, the application retrieves the instruction files from the mobile application or from the remote server and presents the instructions to the user, as described hereinabove with respect to FIG. 23.

Figure 25:
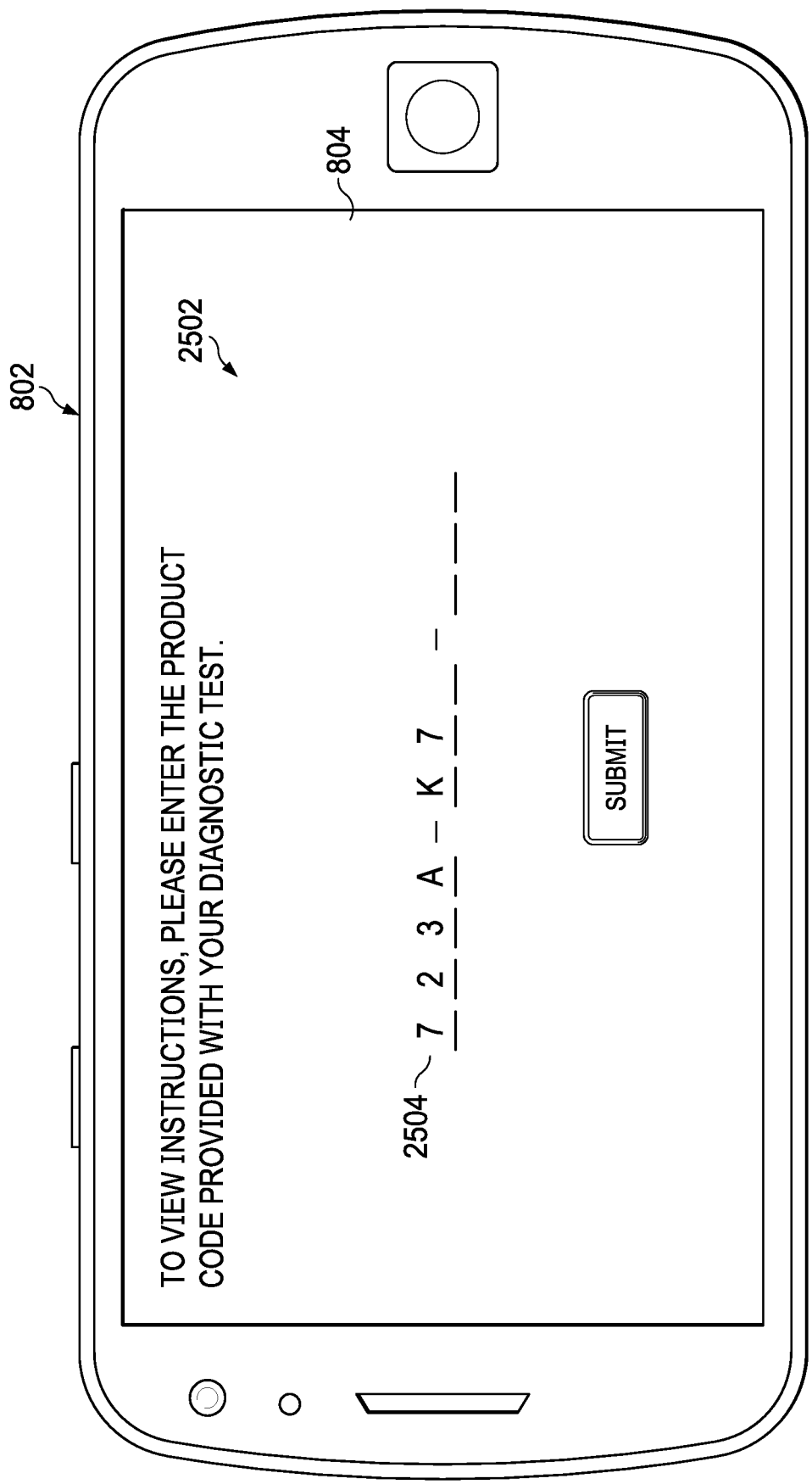
FIG. 25 illustrates a process for entering a product code into a mobile device on a mobile application for the purpose of obtaining instructions for a self-diagnostic test.

Turning now to FIG. 25, there is illustrated another embodiment in which instructions for the diagnostic test are presented in an audio or video format by the mobile application. In these embodiments, rather than the user scanning a product code to inform the mobile application which set of instructions to present as described hereinabove with respect to FIG. 24, the user inputs a code into the application. In these embodiments, a menu 2502 is presented on the screen 804 which allows the user to input an alphanumeric product code 2504 made of a combination of numbers and/or letters which indicate to the mobile application which instructions need to be presented. The alphanumeric product code 2504 may be printed on the packaging for the test, on documentation included with the test, or even on components of the test itself. Once the alphanumeric product code 2504 is input into the mobile application, the mobile application accesses the database as described hereinabove with respect to FIG. 24 to retrieve or access the correct instructions to be presented to the user.

Figure 26:
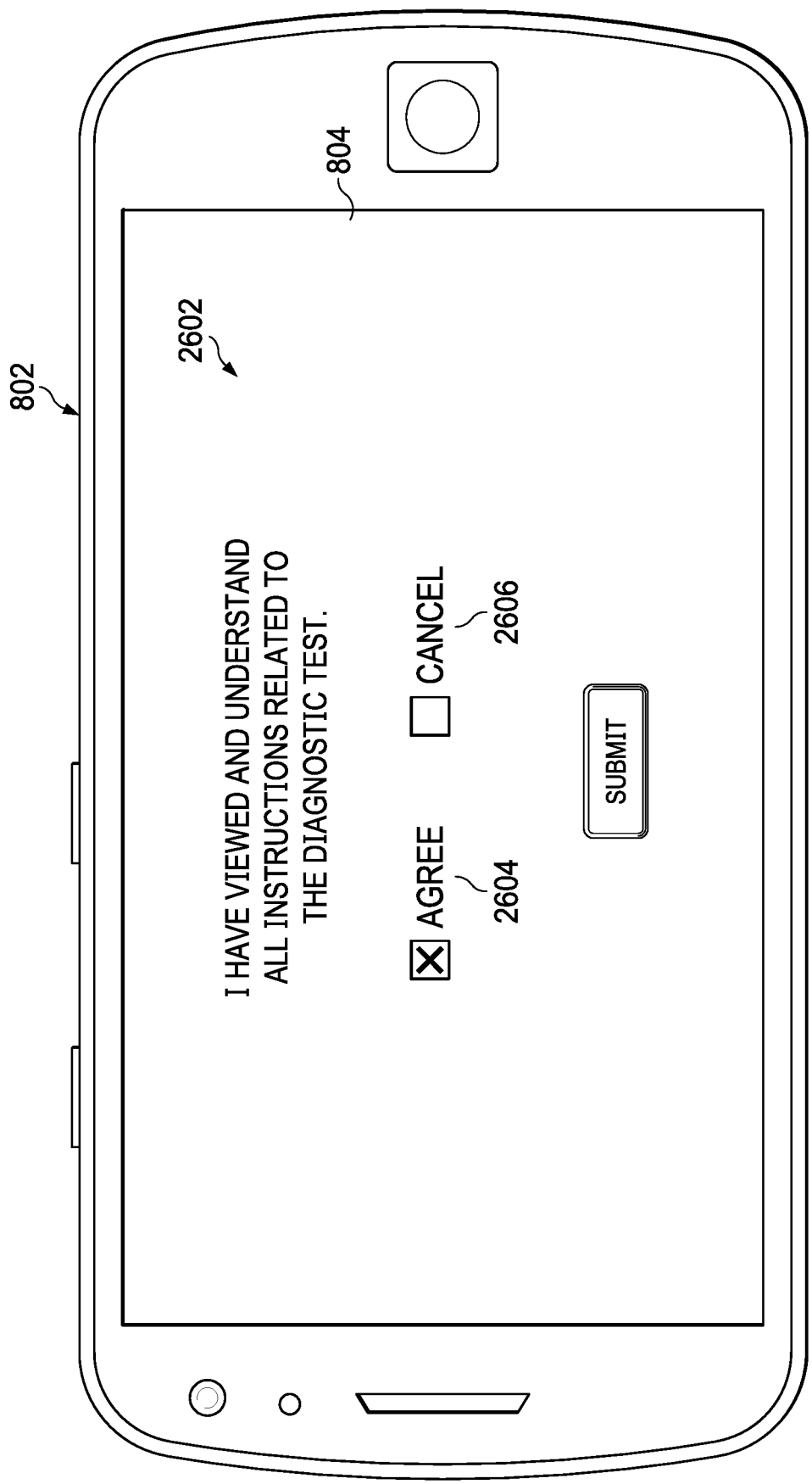
FIG. 26 illustrates an acknowledgement screen on a mobile application for a user to acknowledge understanding self-diagnostic test instructions.

Turning now to FIG. 26, there is illustrated an embodiment in which the mobile application helps ensure that the instructions for the self-diagnostic test have been presented to the user. As discussed hereinabove with respect to FIG. 23, it is important, for various reasons, for the user of the test to fully understand the proper way to administer the test. To help ensure that the proper instructions for the test have been presented to the user, some embodiments include a feature which requires the instructions to be fully presented and for the user to acknowledge understanding the instructions. In these embodiments, the instructions for the diagnostic test are presented by the mobile application to the user in the manner described hereinabove with respect to FIGS. 23-25. The video or audio instructions must be presented in their entirety before the mobile application will allow the user to proceed to the part of the application in which the user captures an image of the testing device 300 to obtain a test result. Once the instructions have been fully presented to the user, the mobile application presents an acknowledgement menu 2602 to the user on the screen 804 of the mobile device 802. This acknowledgement menu 2602 requires the user to acknowledge that he has viewed (or listened) to the instructions and understands how to administer the self-test. The mobile application will not proceed to the step wherein the user captures an image of the testing device for image processing until the user acknowledges viewing (or listening to) and understanding the instructions. From the acknowledgment menu, the user can either select the option 2604 acknowledging he has viewed (or listened to) and understands the instructions, sending the application to the test device image capturing steps described hereinabove with respect to FIGS. 23-25, or the user can select the option 2606 which declines to acknowledge understanding the instructions. Selecting that option 2606 will cause the mobile application to re-present the instructions as described hereinabove with respect to FIG. 23, or cause the mobile application proceed to some stage of the application other than the test device image capturing stage.

Figure 27:
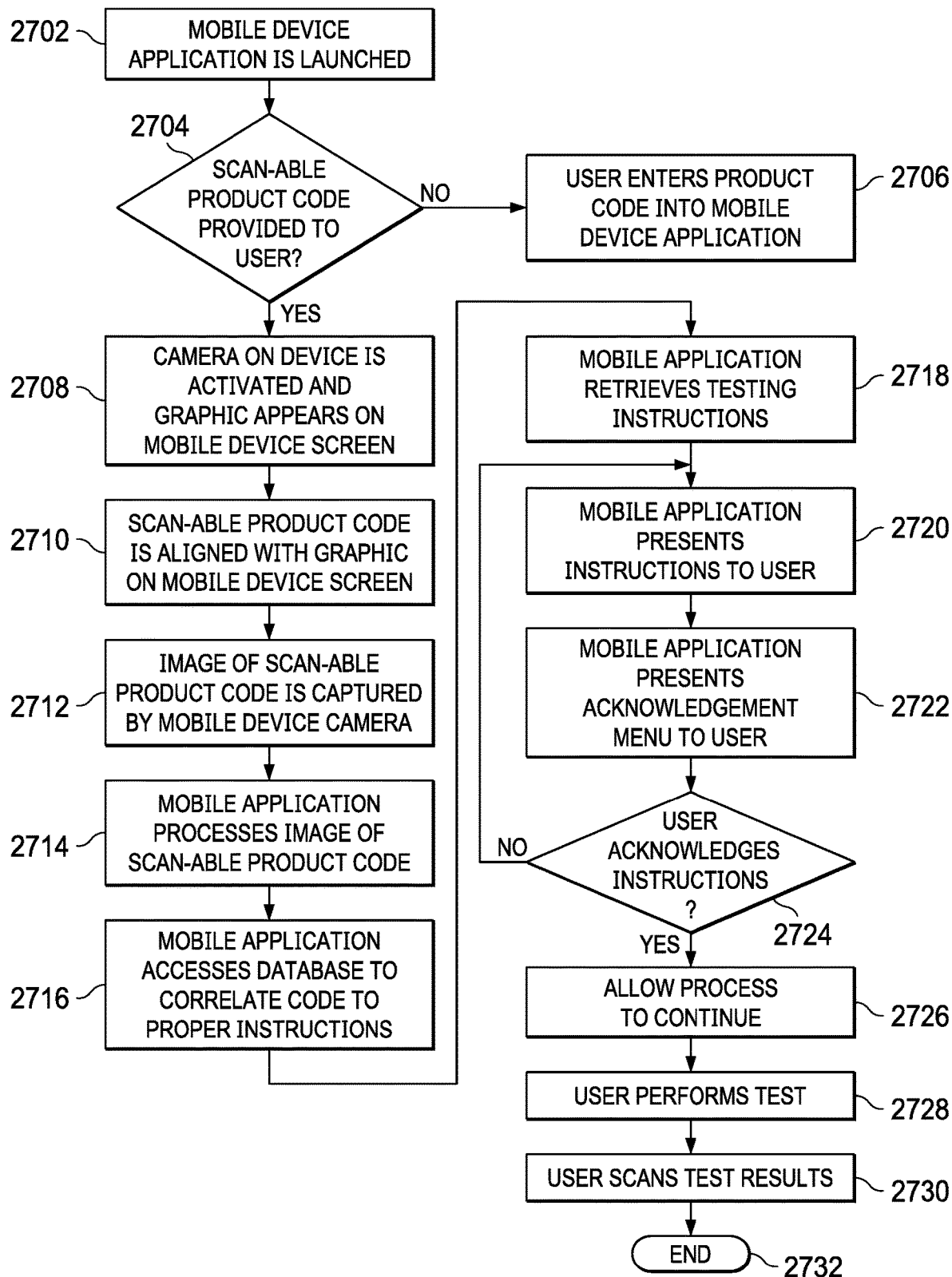
FIG. 27 illustrates a flowchart depicting a process for presenting self-diagnostic test instructions to a user.

Turning now to FIG. 27, there is illustrated a flowchart showing the process by which instructions are presented to the user via the mobile application. The process starts at block 2702, where the user starts the mobile application on the mobile device 802. The process then moves to decision block 2704. If the product code provided to the user is not a scan-able product code 2402, then the process moves to block 2706, where the user enters an alphanumeric product code 2504 into a menu 2502. The process then moves to block 2716, where the mobile application accesses a database and correlates the alphanumeric product code 2504 to the proper test instructions. If, at decision block 2704, the product code provided to the user is a scan-able product code 2402, the process instead moves to block 2708. Here, the camera on the mobile device 802 is activated, and an alignment graphic 2404 appears on the screen 804. Next, the process moves to block 2710, where the scan-able product code 2402 is aligned with the graphic on the mobile device screen 804 by the user. The process then moves to block 2712, where the mobile application causes the mobile device camera to capture an image of the scan-able product code 2402. Next, at block 2414, the mobile application processes the image of the scan-able product code 2402 and processes it into a format which will be correlated with the database of instructions. The process then moves to block 2716, where the mobile application on the mobile device 802 accesses a database, locally or on a remote server, and correlates the formatted code to the proper instruction set in the database. Next, at block 2718, the mobile application retrieves the proper instruction files, either from the mobile device 802 or from a remote server via the internet. The process then moves to block 2720, where the instructions are presented to the user in either video or audio format. Next, the process moves to block 2722, where the application presents an acknowledgement menu 2602 to the user so that the user can acknowledge understanding the instructions. The process moves to decision block 2724, where, ff the user does not acknowledge understanding the instructions, the process loops back to block 2720, where the instructions are again presented to the user. If the user acknowledges the instructions, the process moves to block 2726, where the mobile application allows the user to continue. The process moves to block 2728, where the user performs the self-diagnostic test, per the given instructions. The process then moves to block 2730, where the user scans the testing device 300 for results analysis. The process then ends at End block 2732.

It should be noted that, in some embodiments, the user will be taken to parts of the mobile application other than the playing of the instructions if the user declines to acknowledge understanding the instructions. For example, the mobile device 802 could present the user with a screen that reminds the user that the test cannot proceed until the user acknowledges understanding the instructions. The mobile application then gives the user another chance to acknowledge the instructions. Or, in other embodiments, the mobile application returns the user to the portion of the application where the user scans or inputs a code to allow the application to retrieve the correct instruction files.

In some embodiments, when the user acknowledges understanding the test instructions, a file or data log will be created to document that the user acknowledged understanding the test instructions. The log will include information such as the time at which the instructions were acknowledged, which diagnostic test the instructions were for, or which biologic ID the acknowledgement will be associated with. In some embodiments, the acknowledgement log is stored on the mobile device 802 in the mobile application software, while in other embodiments, the acknowledgement log is transmitted to a remote server for storage and record-keeping.

Figure 28:
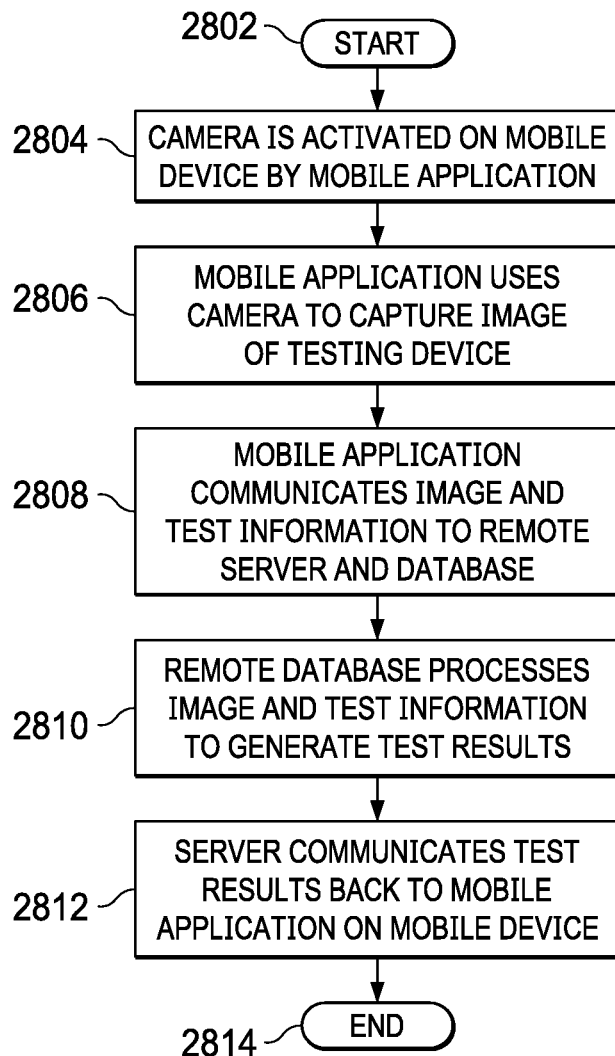
FIG. 28 illustrates a flowchart for generating test results with a remote server and database from an image communicated by a mobile application on a mobile device.

Turning now to FIG. 28, there is illustrated a flowchart for embodiments in which the image of the testing device 300 is processed by a database on a remote server, rather than by the mobile application itself running on the mobile device 802. These embodiments are useful for when a mobile application is capable of working with multiple different tests such that storing information and data needed to process several different types of tests might consume more data storage on a single mobile device than is practical or desirable. The process starts at Start block 2802, after the user has deposited the biologic sample into the testing device 300 and any chemical reactions have occurred. The process then moves to block 2804, where the mobile application activates the camera on the mobile device 802. The process moves to block 2806, where the user uses the mobile application to capture an image of the testing device 300 with the mobile device 802 camera. Next, at block 2808, the mobile application communicates over the internet the image of the testing device 300, along with information identifying the type of test being conducted, to a remote server and database for analysis. At block 2810, the database analyzes the received test information and image and generates test results. This step is analogous to the steps described hereinabove with respect to FIGS. 9, 11 and 14, except that the image analysis takes place on a remote server and database, rather than on the mobile device itself. The process then moves to block 2812, where the server communicates the test results back to the mobile application running on the mobile device 802. The process then ends at block 2814.

Figure 29:
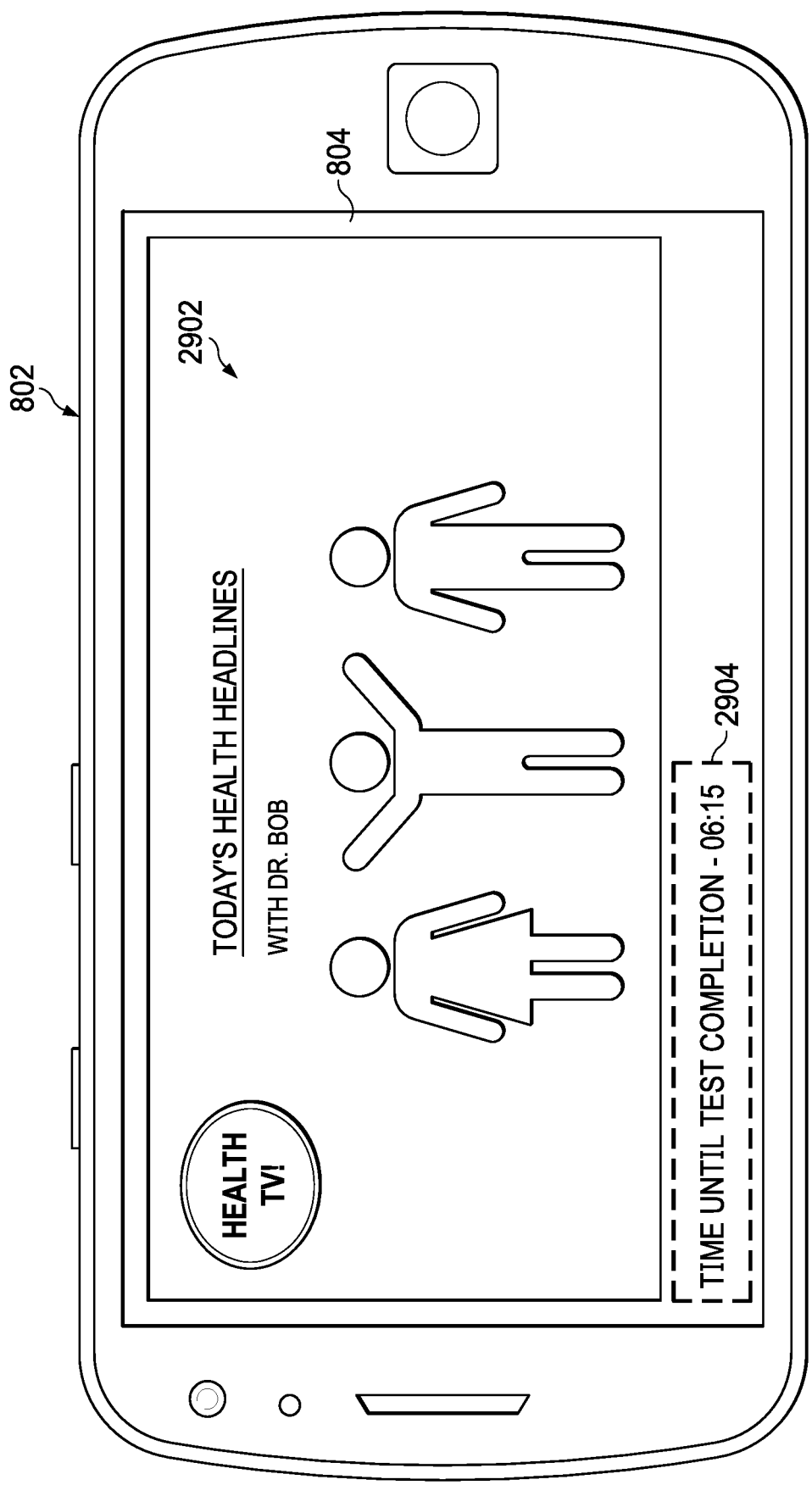
FIG. 29 illustrates a mobile device displaying audiovisual messages to a self-diagnostic test user.

Turning now to FIG. 29, there is illustrated a mobile device 802 from an embodiment which includes delivering audiovisual messages to a self-diagnostic test user in response to the user performing the test and submitting the test for results. After a biologic sample 204 is placed within the testing device 300, a certain amount of time is required for the sample to migrate into the various parts of the strip or strips 204, for any chemical reaction to occur, and for any visual indicators to appear in the testing device 300. During this time, the user is somewhat of a "captive audience," in that he will likely be focused on the test and the mobile application, rather than other aspects of daily life, while he is waiting for the test to be completed. This means that content providers of audiovisual messages know that their content is more likely to be paid attention to by the mobile application user. This, in turn, means that content presented to users can demand a premium price. Some embodiments of the system, such as that illustrated in FIG. 29, take advantage of the user being a "captive audience" and allow the mobile application to present targeted audiovisual messages 2902 to the user. This occurs during the time between the user placing the biologic sample 204 in the testing device 300 and the time when the testing device is ready to have its image captured by the camera for analysis by the mobile application or remote server. In some embodiments, the targeted audiovisual messages 2902 are in the form a "TV channel" which provides health-related content and programming. This programming can include long-format video messages 2902 that are approximately thirty minutes in length such as might be found on a traditional TV channel and can resemble television shows or info-mercials. The programming can also include audiovisual messages 2902 in the form of shorter video segments that are anywhere between one minute and five minutes in length. Some embodiments will present the same audiovisual messages 2902 to all users, regardless of which diagnostic test the user is performing. In other embodiments, the specific audiovisual messages 2902 presented to a particular user will depend on which diagnostic test the user is using. For example, if a user is performing a pregnancy test, the audiovisual messages 2902 will be related to babies or pregnancy. If a user is performing an HIV test, the audiovisual messages 2902 delivered to the user will be related to HIV treatment and management. Audiovisual messages 2902 can be created that relate to any of the types of tests found in various embodiments of the system.

Some embodiments will also include a countdown clock 2904. The countdown clock 2904 is presented on the mobile device screen 804 while the biologic is moving through the test device 300 and any chemical reactions are occurring, which is also when audiovisual messages 2904 are being presented to the user. The countdown clock 2904 displays the time until the test device 300 is ready to be photographed by the camera for processing by the mobile application or remote server. The inclusion of a countdown clock 2904 is another tool which helps keep the user focused on the mobile application while the audiovisual messages 2902 are being presented. In some embodiments, a countdown clock 2904 is presented to the user after any reactions have occurred and an image of the test device 300 has been captured by the camera. In these embodiments, the countdown clock 2904 displays the time left until the test device image is processed by the mobile application or the remote server and a result is delivered and presented to the user. The countdown clock 2904 is started by the user indicating through a menu that he has placed a biologic sample in the testing device 300. It should be noted that the countdown clock 2904 is related to the time left for the reaction to complete (or the test device image to be processed), but in some embodiments, additional time is added to the countdown clock beyond just the completion time of the reaction or the image processing. In these embodiments, the countdown clock 2904 begins when the user photographs the testing device 300 for results analysis. Different types of self-diagnostic tests will have different test completion times. These times are stored in a database in the mobile application, or, in some embodiments, on a remote server which communicates the testing times to the mobile application.

In some embodiments, the audiovisual messages 2902 are presented to the user after the mobile device 802 camera has captured an image of the test device 300 for processing by the mobile application or the remote server and database. In these embodiments, the audiovisual messages 2902 that are presented after the user captures a test device 300 image are in addition to audiovisual messages presented while the user is waiting for any chemical reactions to take place in the test device before the image is captured. In still other embodiments, audiovisual messages 2902 are presented only after the image of the test device 300 is captured and is being processed by the mobile application or the remote server and database.

Figure 30:
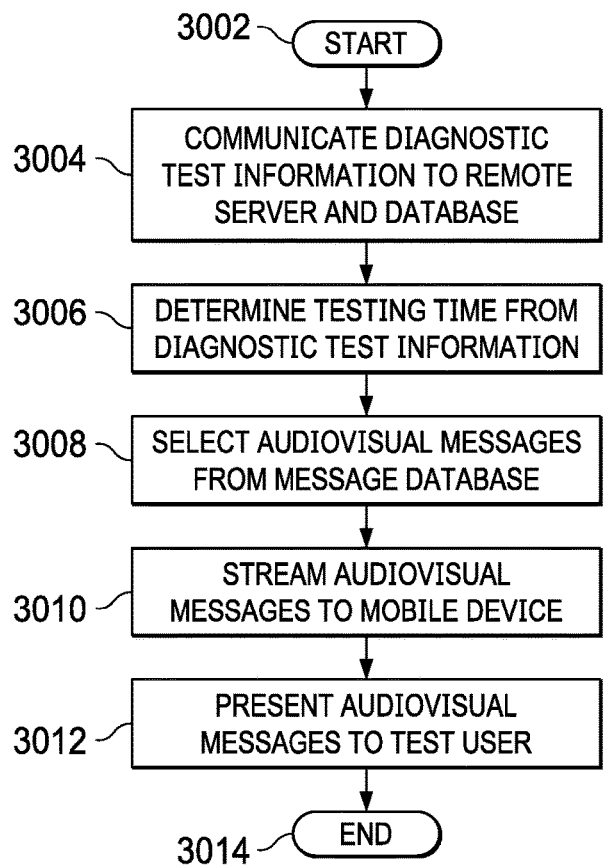
FIG. 30 illustrates a flowchart depicting a process for presenting audiovisual messages to a self-diagnostic test user.

Turning now to FIG. 30, there is illustrated a flowchart for the process of streaming audiovisual messages 2902 to a mobile application on a mobile device 802. In some embodiments, the audiovisual messages 2902 are stored on the mobile device 802 itself. Preferably, however, the audiovisual messages 2902 are stored on a remote message database and then streamed by a server to the mobile device 802 which is running the mobile application. The process starts at block 3002 and proceeds to block 3004, where the mobile application communicates information about the diagnostic test to the remote servers. This information notifies the server and database that the user is performing a diagnostic test and that the mobile application is ready to stream audiovisual messages 2902 to the user. For embodiments in which the audiovisual messages 2902 that are presented to the user are specific to the type of diagnostic test the user is performing, this information also includes information identifying the specific type of self-diagnostic test. Next, the process moves to block 3006, where the testing time is determined from the diagnostic test identification information. In some embodiments, the testing time is communicated to the mobile application from a remote server, while in other embodiments, this time is stored in a database within the mobile application. Next, at block 3006, an appropriate audiovisual message 2902 or set of messages is selected from a message database. For embodiments which present specific messages 2902 to users of specific diagnostic tests, the test-identifying information is used by the database to select a message related to the type of test being used. The process then moves to block 3008, where the remote server streams the audiovisual messages 2902 to the mobile device 802 running the mobile application. Next, at block 3010, the mobile application presents the audiovisual messages 2902 to the user. The process ends at block 3012.

Figure 31:
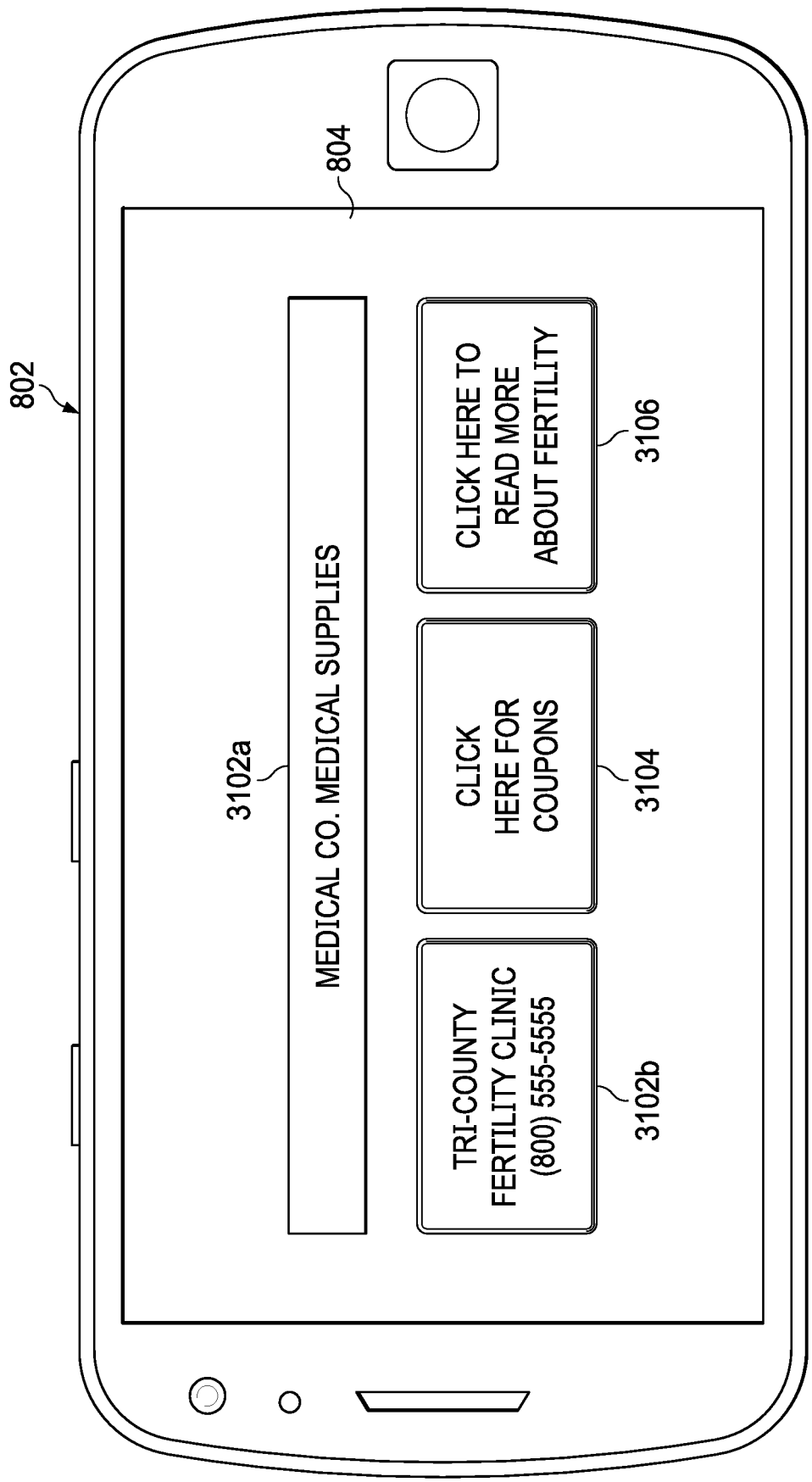
FIG. 31 illustrates a mobile device presenting a variety of types of advertisements to a self-diagnostic test user.

Referring now to FIG. 31, there is illustrated a mobile device 802 from an embodiment in which video or visual advertisements are presented to the user in response to the user performing a self-diagnostic test. In these embodiments, the knowledge that the user has purchased and/or is performing a self-diagnostic medial test is used to deliver targeted advertisements 3102 to the user through the mobile application. Some embodiments store the files for the advertisements 3102 within the mobile application, while other embodiments allow the mobile application to stream or send the advertisements from a remote server. The targeted advertisements 3102 are presented to the user on the screen 804 of the mobile device 802 at different stages throughout the testing process. In some embodiments, the targeted advertisements 3102 will include generic advertisements 3102*a* which are delivered to all users of the mobile application. These advertisements 3102*a* are targeted at users of medical self-diagnostic tests generally, but are not specific to the type of test. Other embodiments will include targeted advertisements 3102*b* which are directed at users of specific types of self-diagnostic tests. For example, a user who is performing a pregnancy test may see an advertisement 3102*b* for a fertility clinic. As another example, a user who is performing a test for celiac disease may be presented with an advertisement for a brand of gluten-free food. Some embodiments will include advertisements in the form of electronic coupons 3104. These electronic coupons 3104 allow users to "click" the coupon image on the mobile device screen 804 to receive coupons for health-related products and services. Different embodiments will allow users to receive coupons in different forms, such as redemption codes, physical coupons via mail, or computer readable images. Similar to the targeted advertisements 3102, some embodiments will present the same electronic coupons 3104 to all users of the mobile application, while other embodiments will present different electronic coupons to users based on the type of diagnostic test being performed. Some embodiments also include advertisements in the form of informational links 3106 to various websites. These informational links 3106 present users with links to websites featuring informative literature or videos related to health issues and medical testing. Again, some embodiments will feature generic informational links 3106 common to all users of the mobile application, while other embodiments will present specific informational links to users of specific types of diagnostic tests.

As discussed hereinabove, the various types of advertisements 3102, 3104, 3106 can be presented to the user at different stages throughout the testing process. In some embodiments, the advertisements 3102, 3104, 3106 are presented when the user starts the mobile application. In other embodiments, the advertisements 3102, 3104, 3016 are presented to the user when an image is scanned or a code is input by the user identifying the type of diagnostic test to the mobile application. In still other embodiments, the advertisements 3102, 3104, 3106 are presented to the user after the results of the test have been delivered to the user. Other embodiments will present the advertisements 3102, 3104, 3106 at other acceptable points in the testing process.

Figure 32:
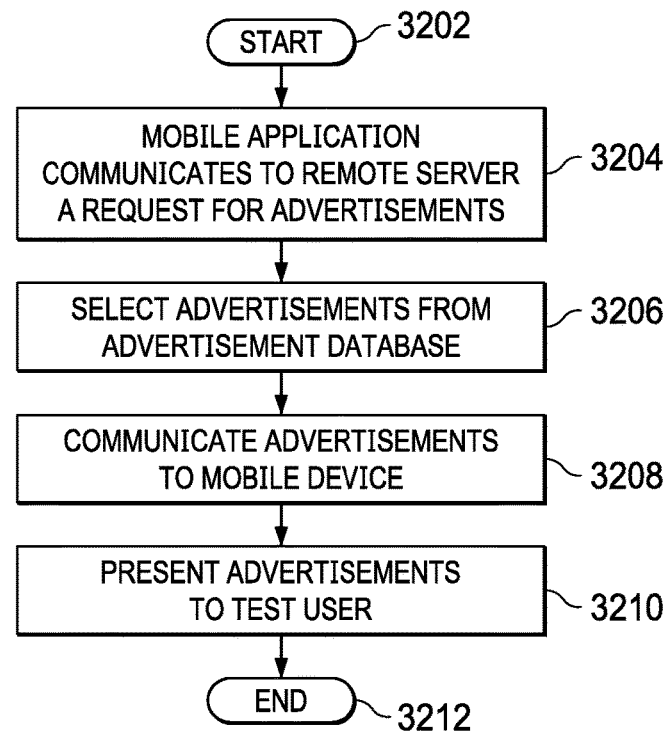
FIG. 32 illustrates a flowchart depicting a process for presenting advertisements to a self-diagnostic test user.

Turning now to FIG. 32, there is illustrated a flowchart which depicts the process for transmitting advertisements for embodiments in which the application downloads the advertisements 3102, 3104, 3106 from a remote server before presenting them to the user. The process starts at Start block 3202 and proceeds to block 3204. At function block 3204, the mobile application communicates to the server that a request for advertisements 3102, 3104, 31016 to present to the user. In embodiments in which the specific advertisement 3102, 3104, 3106 depends on what type of diagnostic test is being performed, the mobile application also communicates to the server information identifying the type of test. The process then moves to block 3206. At block 3206, the server accesses a storage database where the advertisements are stored and communicates the advertisements to the mobile device 802 running the mobile application. In embodiments which take into account the type of test being performed, the server selects appropriate advertisements 3102, 3104, 3106 from a database of advertisements based on the test identification information sent by the mobile application. The process then moves to block 3208, where the files for the advertisements 3102, 3104, 3106 are communicated by the remote server to the mobile application on the mobile device. The process then moves to block 3210, where the mobile application presents the advertisements 3102, 3104, 3106 to the user. The process then ends at End block 3212.

Figure 33:
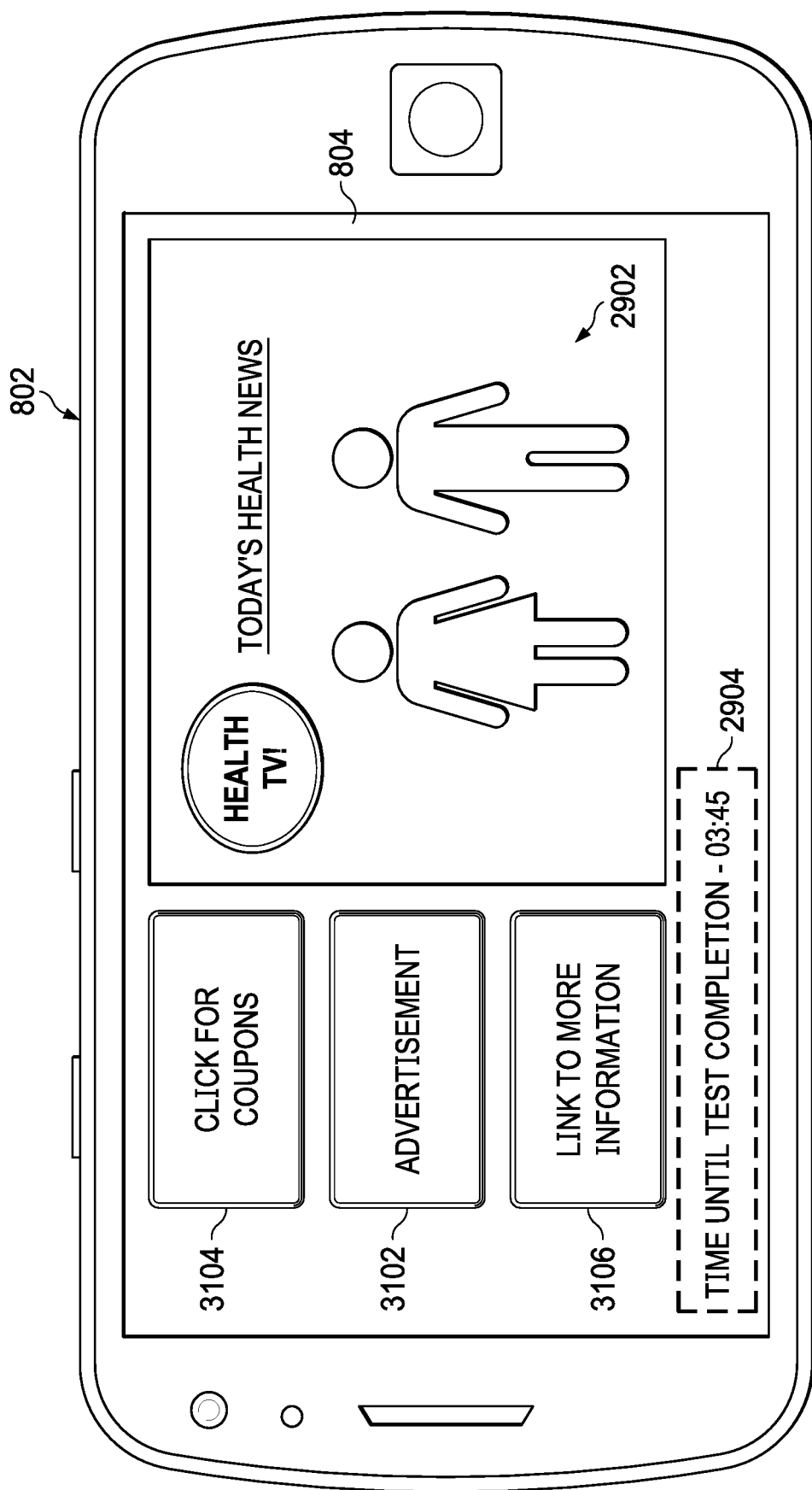
FIG. 33 illustrates a mobile device presenting audiovisual messages and advertisements to a self-diagnostic test user.

Turning now to FIG. 33, there is illustrated an embodiment which displays advertisements along with audiovisual messages. These embodiments include the audiovisual messages 2902 as described hereinabove with respect to FIG. 29. However, these embodiments also include advertisements 3102, 3104, 3106 displayed on the screen 804 at the same time as the audiovisual messages 2902 are displayed, such as when the user is waiting for chemical reactions in the test to occur or for the processing of a test device image to complete. When advertisements 3102, 3104, 3106 are presented, they may be related to the audiovisual message 2902 also being displayed. For example, if the audiovisual message 2902 features actors discussing a particular medical or health product, the targeted advertisement 3102 could be an advertisement for that product. Or, if the audiovisual message 2902 features a short segment from a broadcast television show, the informative link 3106 could be a link to the website of the television show.

It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A method of a mobile device for providing advertising audiovisual messages in response to an input related to a medical testing device, the method comprising:
   generating a display interface on a viewing screen of the mobile device of a user interface including an alignment graphic;
   detecting an alignment of the alignment graphic on the display interface and a scannable code on the medical testing device;
   actuating a camera to capture an image of the medical testing device in response to the detected alignment of the alignment graphic on the display interface and the scannable code on the medical testing device;
   transmitting diagnostic test information including the captured image and the scannable code to a remote server and an associated at least one database storing information relating to the medical testing device and a plurality of advertising audio visual messages related to multiple medical tests;
   receiving, from the remote server, a determined testing time, the determined testing time determined at the remote server based on the scannable code, and at least one advertising audio visual message having a length in a range that was selected responsive to the determined testing time and the diagnostic test information from the plurality of advertising audio visual messages related to multiple medical tests;
   generating a video display window within the display interface responsive to the received at least one advertising audio visual message;
   displaying, in the display interface on the viewing screen of the mobile device, the at least one advertising audio visual message having the length in the range selected responsive to the determined testing time and the diagnostic test information in the video display window responsive to its receipt at the mobile device;
   generating a timer indication for processing of the diagnostic test information responsive to the received determined testing time;
   displaying the timer indication within a test timer window of the display interface adjacent to the video display window;
   updating the timer indication within the test timer window to display a countdown based on the determined testing time; and
   wherein a length of the determined at least one at least one advertising audio visual message received from the remote server is responsive to the determined testing time.

2. The method of claim 1, further comprising presenting a menu on the viewing screen of the mobile device which provides a user with an option to acknowledge comprehending a first portion of the at least one advertising audio visual message.

3. The method of claim 2, further comprising presenting, after the user has selected the option to acknowledge comprehending the first portion of the at least one advertising audio visual message, second portion of the at least one advertising audio visual message.

4. The method of claim 1, further comprising:
   presenting a test result on the viewing screen of the mobile device.

5. The method of claim 1, further comprising:
   providing a risk indicator alerting a user to seek medical attention immediately.

6. A system for providing audiovisual messages in response to an input, the system comprising:
   a medical testing device having thereon a scannable code;
   a mobile device having a camera, a viewing screen, and a software application stored thereon, wherein the software application provides executable instructions to:
      generating a display interface on the viewing screen of the mobile device of a user interface including an alignment graphic;
      detect an alignment of the alignment graphic on the display interface and the scannable code on the medical testing device;
      actuate the camera to capture an image of the medical testing device in response to the detected alignment of the alignment graphic on the display interface and the scannable code on the medical testing device;
      transmit diagnostic test information including the captured image and the scannable code;
   a remote server including a second software application and at least one database for storing information relating to the medical testing device and a plurality of advertising audio visual messages related to multiple medical tests, wherein the second software application provides executable instructions to:
      receive the diagnostic test information including the captured image and the scannable code;
      determine a testing time for the medical testing device based on the scannable code and stored information within the at least one database relating to the medical testing device;
      selecting at least one advertising audio visual message from the plurality of advertising audio visual messages related to multiple medical tests having a length in a range that is responsive to the determined testing time and the diagnostic test information;
      transmit the determined testing time for the medical testing device and the selected at least one advertising audio visual message to the mobile device;
   wherein the software application of the mobile device further provides executable instructions to:
      receive the determined testing time based on the diagnostic test information and the at least one advertising audio visual message based on determined testing time and the diagnostic test information;
      generate a video display window within the display interface responsive to the received at least one advertising audio visual message having a length selected based on the determined testing time;
      display, in the display interface on the viewing screen of the mobile device, the at least one advertising audio visual message having a length selected based on the determined testing time in the video display window responsive to it receipt at the mobile device;
      generate a timer indication for processing of the diagnostic test information responsive to the received determined testing time;

display the timer indication within a test timer window of the display interface adjacent to the video display window;

periodically update the timer indication within the test timer window to display a countdown based on the determined testing time.

7. The system of claim 6, wherein the software application further provides executable instructions to:

present a menu on the viewing screen of the mobile device which provides a user with an option to acknowledge comprehending a first portion of the at least one advertising audio visual message.

8. The system of claim 7, wherein the software application further provides executable instructions to:

present, after the user has selected the option to acknowledge comprehending the first portion of the at least one advertising audio visual message, a second portion of the at least one advertising audio visual message.

9. The system of claim 6, wherein the software application further provides executable instructions to:

present a test result on the viewing screen of the mobile device.

10. The system of claim 6, wherein the software application further provides executable instructions to:

provide a risk indicator alerting a user to seek medical attention immediately.

11. An apparatus for providing advertising audiovisual messages in response to an input from a medical testing device, comprising:

at least one database storing information related to the medical testing device including testing times associated with the medical testing device and a plurality of advertising audio visual messages related to multiple medical tests;

a mobile device having a camera, a viewing screen, and a software application stored thereon;

wherein the software application provides executable instructions to:

receive an identifier for the medical testing device that identifies a test being performed;

determine a period of time for completion of a test process by the medical testing device by accessing the at least one database responsive to the identifier for the medical testing device;

receive an indication that the test process has been initiated with the medical testing device;

actuating a timer to countdown the period of time for completion of the test process responsive to the indication;

receive at least one advertising audio visual message responsive to the identifier for the medical testing device, the at least one advertising audio visual message having a length within a range selected responsive to the determined period of time for completion of the test process from the plurality of advertising audio visual messages related to multiple medical tests;

generating a display interface of a video display window within the viewing screen of the mobile device responsive to the received at least one advertising audio visual message having the length within the range selected responsive to the determined period of time for completion of the test process; and displaying within the video display window of the display interface the at least one advertising audio visual message having the length within a range selected responsive to the determined period of time for completion of the test process in the video display window within the viewing screen of the mobile device.

12. The apparatus of claim 11, wherein the software application provides executable instructions to:

generate a timer indication for the period of time for completion of the test process responsive to the indication that the test process has been initiated; and displaying the timer indication within a test timer window adjacent to the video display window.

13. The apparatus of claim 11, wherein the at least one database is located at a remote server.

14. The apparatus of claim 11, wherein the software application provide executable instructions to:

display, on the viewing screen of the mobile device, a user interface including an alignment graphic;

detect an alignment of the alignment graphic and a scannable code on the medical testing device;

capture an image of the medical testing device in response to the detected alignment;

determine a second period of time for processing the image of the medical testing device responsive to receipt of the captured image;

actuating the timer to countdown the determined second period of time for processing the image of the medical testing device;

receive the at least one advertising audio visual message responsive to the captured image, the at least one advertising audio visual message having a length responsive to the determined second period of time for processing the image of the medical testing device; and displaying the at least one advertising audio visual message in the video display window within the viewing screen of the mobile device during performance of the test process by the medical testing device.

\* \* \* \* \*